United States Patent
Mabire et al.

(10) Patent No.: US 8,524,714 B2
(45) Date of Patent: *Sep. 3, 2013

(54) 7-PHENYLALKYL SUBSTITUTED 2-QUINOLINONES AND 2-QUINOXALINONES AS POLY(ADP-RIBOSE) POLYMERASE INHIBITORS

(75) Inventors: Dominique Jean-Pierre Mabire, Val de Reuil (FR); Jerome Emile Georges Guillemont, Val de Reuil (FR); Jacobus Alphonsus Josephus van Dun, Tielen (BE); Maria Victorina Francisca Somers, Vosselaar (BE); Walter Boudewijn Leopold Wouters, Kapellen (BE)

(73) Assignee: Janssen Pharmaceutica, NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/047,402

(22) Filed: Mar. 14, 2011

(65) Prior Publication Data

US 2011/0230492 A1 Sep. 22, 2011

Related U.S. Application Data

(62) Division of application No. 10/595,882, filed as application No. PCT/EP2004/013162 on Nov. 18, 2004, now Pat. No. 7,928,104.

(30) Foreign Application Priority Data

Nov. 20, 2003 (EP) .................................. 03078650

(51) Int. Cl.
*A61K 31/498* (2006.01)
*C07D 401/06* (2006.01)

(52) U.S. Cl.
USPC ........................... 514/249; 544/354; 514/312

(58) Field of Classification Search
None
See application file for complete search history.

(56) References Cited

U.S. PATENT DOCUMENTS

| | | | |
|---|---|---|---|
| 3,274,194 A | 9/1966 | Hayao et al. | |
| 3,753,988 A | 8/1973 | Rodway et al. | |
| 3,879,393 A | 4/1975 | Havera | |
| 3,919,425 A | 11/1975 | Vidrio | |
| 4,335,127 A | 6/1982 | Vandenberk et al. | |
| 5,028,606 A * | 7/1991 | Venet et al. .................. | 514/249 |
| 5,118,684 A | 6/1992 | Sugimoto et al. | |
| 5,151,421 A | 9/1992 | Venet et al. | |
| 5,177,075 A | 1/1993 | Suto et al. | |
| 5,231,184 A | 7/1993 | Stokbroekx et al. | |
| 5,304,560 A | 4/1994 | Shimazaki et al. | |
| 5,374,637 A | 12/1994 | Van Daele et al. | |
| 6,344,449 B1 | 2/2002 | Rudolf et al. | |
| 6,635,642 B1 | 10/2003 | Jackson et al. | |
| 7,115,630 B2 | 10/2006 | Mabire et al. | |
| 7,498,325 B2 | 3/2009 | Rudolf et al. | |
| 7,928,104 B2 | 4/2011 | Mabire et al. | |
| 8,198,448 B2 | 6/2012 | Albrecht et al. | |
| 2001/0036946 A1 | 11/2001 | Rudolf et al. | |
| 2002/0002174 A1 | 1/2002 | Nieduzak et al. | |
| 2003/0069231 A1 | 4/2003 | Rudolf et al. | |
| 2003/0130505 A1 | 7/2003 | Zhi et al. | |
| 2003/0225268 A1 | 12/2003 | Bunnelle et al. | |
| 2004/0077667 A1 | 4/2004 | Matsuoka et al. | |
| 2004/0176361 A1 | 9/2004 | Fujio et al. | |
| 2005/0256000 A1 | 11/2005 | Schaper et al. | |
| 2008/0039480 A1 | 2/2008 | Kennis et al. | |
| 2008/0269234 A1 | 10/2008 | Gandhi et al. | |
| 2009/0048259 A1 | 2/2009 | Austin et al. | |
| 2009/0163480 A1 | 6/2009 | Rudolf et al. | |
| 2009/0292121 A1 | 11/2009 | Morioka et al. | |
| 2012/0046274 A1 | 2/2012 | Mabire et al. | |

FOREIGN PATENT DOCUMENTS

| | | |
|---|---|---|
| DE | 1006423 | 4/1957 |
| DE | 2258561 A | 6/1973 |
| EP | 0013612 B1 | 11/1983 |
| EP | 0156433 | 10/1985 |
| EP | 0229391 A1 | 7/1987 |
| EP | 0371564 B1 | 6/1990 |
| EP | 0391462 A1 | 10/1990 |
| EP | 0638567 | 2/1995 |
| EP | 0669919 B1 | 9/1995 |
| EP | 1026160 A1 | 8/2000 |
| EP | 0885190 B1 | 5/2003 |
| FR | 2436781 | 5/1980 |

(Continued)

OTHER PUBLICATIONS

Peters et al. (Pharmacology & Therapeutics, 87:227-253, 2000).*
PCT Intl. Search Report, PCT/EP2004/013162, Mar. 18, 2005.
Ali et al., "Synthesis and Antimicrobial Activities of Some Novel Quinoxalinone Derivatives", *Molecules*, 2000, pp. 864-873, vol. 5, No. 6, 'Online Computer File'.
Kulcsar et al., "Synthesis and Study of New 4-Quinazolinone Inhibitors of the DNA Repair Enzyme Poly (ADP-ribsose) Polymerase (PARP)", *ARKIVOC*, XX,XX, Jun. 11, 2003, pp. 121-123, vol. 2003, No. Part V, XP002291367.
Li et al., "PARP Inhibitors", *IDrugs*, 2001, pp. 804-812, vol. 4, No. 7, Current Drugs Ltd., GB.
Weltin et al., "Effect of 6(5-Phenanthridinone, an Inhibitor of Poly(ADP-ribose) Polymerase, on Cultured Tumor Cells", *Oncology Research*, 1994, pp. 399-403, Vo.l. 6, No. 9, Elsevier Science Ltd., USA.
"Cancer definition", http://www.medterms.com/script/main/art.asp?articlekey=2580, accessed Nov. 27, 2007.
"Prostate Cancer Prevention", http://www.cancer.gov/cancertopics/pdq/prevention/prostate/Patient, accessed Apr. 9, 2010.

(Continued)

*Primary Examiner* — Bong-Sook Baek

(57) ABSTRACT

The present invention provides compounds of formula (I), their use as PARP inhibitors as well as pharmaceutical compositions comprising said compounds of formula (I)

(I)

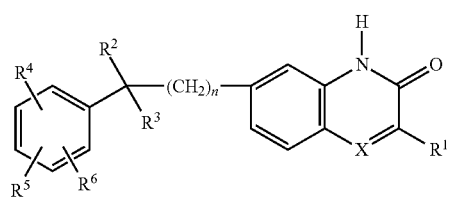

wherein n, $R^1$, $R^2$, $R^3$, $R^4$, $R^5$, $R^6$ and X have defined meanings.

1 Claim, No Drawings

(56) References Cited

FOREIGN PATENT DOCUMENTS

| | | |
|---|---|---|
| GB | 732581 A | 6/1955 |
| GB | 1062357 | 3/1967 |
| JP | 59-076082 | 4/1984 |
| JP | 60-120872 | 6/1985 |
| JP | 60-226862 | 11/1985 |
| JP | 62-234065 | 10/1987 |
| JP | 10007572 | 1/1998 |
| JP | 10-330377 | 12/1998 |
| JP | 2002-515072 | 3/1999 |
| JP | 2000-505100 | 4/2000 |
| JP | 2000191659 | 7/2000 |
| JP | 2002-535409 | 8/2000 |
| JP | 2002284699 | 10/2002 |
| WO | WO 91/12006 A2 | 8/1991 |
| WO | WO 93/22309 A1 | 11/1993 |
| WO | WO 94/19342 A1 | 9/1994 |
| WO | WO 95/24379 A1 | 9/1995 |
| WO | WO 99/11649 A2 | 3/1999 |
| WO | WO 99/29687 A1 | 6/1999 |
| WO | WO 00/44755 A1 | 8/2000 |
| WO | WO 02/28837 A1 | 4/2002 |
| WO | WO 02/36599 A1 | 5/2002 |
| WO | WO 02/48117 A1 | 6/2002 |
| WO | WO 03/015785 A1 | 2/2003 |
| WO | WO 03/039460 A2 | 5/2003 |
| WO | WO 03/055865 A1 | 7/2003 |
| WO | WO 03/080581 A1 | 10/2003 |
| WO | WO 03/082350 A1 | 10/2003 |
| WO | WO 03/101985 A1 | 12/2003 |
| WO | WO 2004/043950 A1 | 5/2004 |
| WO | WO 2005/004801 A2 | 1/2005 |
| WO | WO 2005/054199 A1 | 6/2005 |
| WO | WO 2005/054201 A1 | 6/2005 |
| WO | WO 2005/054210 A1 | 6/2005 |
| WO | WO 2005/058843 A1 | 6/2005 |
| WO | WO 2005/097750 A1 | 10/2005 |
| WO | WO 2005/117876 A1 | 12/2005 |
| WO | WO 2006/003146 A1 | 1/2006 |
| WO | WO 2006/003147 A1 | 1/2006 |
| WO | WO 2006/003148 A1 | 1/2006 |
| WO | WO 2006/003150 A1 | 1/2006 |
| WO | WO 2006/089177 A2 | 8/2006 |
| WO | WO 2007/025009 A2 | 3/2007 |
| WO | WO 2007/087684 A1 | 8/2007 |
| WO | WO 2007/095628 A1 | 8/2007 |
| WO | WO 2008/107478 A1 | 9/2008 |
| ZA | 72/8536 A | 11/1972 |

OTHER PUBLICATIONS

Albert, J.M., et al., "Inhibition of Poly(ADP-Ribose) Polyerase Enhances Cell Death and Improves Tumor Growth Delay in Irradiated Lung Cancer MODels", Clin Cancer Res, (2007), vol. 13, No. 10, pp. 3033-3042.

Ame, J.C., et al., "PARP-2, A Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1H-Pyrrol-1-YL-3-Pyridazinamines", J. Med. Chem., (1984), vol. 27, No. 8 pp. 1077-1083.

Bernard et al., "Automated docking of 82 N-benzylpiperidine derivatives to mouse acetylcholinesterase and comparative molecular field analysis with 'natural' alignment.", Journal of Computer-Aided Molecular Design, 1999, 13(4), pp. 355-371.

Blackburn, W., et al., "The Preparation of 3-Methyl-6- and -7-Carboxy-2- Quinoxalones", Journal of Organic Chemistry, ((1961), vol. 26, pp. 2805-2809.

Bloch, W., et al., "Poly-Adenosine Diphosphate-Ribose Polymerase Inhibition for Myocardial Protection: Pathopysiologic and Physiologic Considerations", Journal of Thoracic and Cardiovascular Surgery, Aug. 2004, vol. 128, No. 2, pp. 323-324.

Bonne, D., et al., "4'6-Diamidino-2-phenylindole, a Fluorescent Probe for Tubulin and Microtubules*", Journal of Biological Chemistry, vol. 260, No. 5 (1985) pp. 2819-2825.

Borisy et al., "Systematic Discovery of Multicomponent Therapeutics.", PNAS, Jun. 24, 2003, pp. 7977-7982, vol. 100(13).

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67.

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

CAS Registry Nos. 464169-24-2, 464169-25-3, 223587-51-7 abstract; figure 24-&JP 2002 284699 A (Sumitomo Pharmaceuticals Co., Ltd., Japan) Oct. 3, 2002.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044.

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82.

Darchen et al., "Ketanserin binds to the monoamine transporter of chromaffin granules and of synaptic vesicles.", Molecular Pharmacology, 1988, 33(6), pp. 672-677.

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93.

Database Ca 'Online! Chemical Abstracts Service, Columbus, Ohio, US; 2002, Tatsuno, Toru et al: "PRP Inhibitors for Treatment of Retinal Degeneration or Chemotherapy-Induced Cell Injury" XP002348719 retrieved from STN Database accession No. 2002:747681.

Database WPI 'Online! Derwent Publications Ltd., London, GB; XP002347462, retrieved from WPI accession No. 1970-18449R, *;see RN 27631-66-9:3-(piperidin-1-yl-propyl)-1H-quinazoline-2,4-dione*, abstract & JP 45007058B (Sankyo) Jul. 6, 1967.

Dörwald, F.Z., "Side Reactions in Organic Synthesis": A Guide to Successful Synthesis Design, Weinheim: Wiley-VCH Verlag GmbH & Co. KGaA, (2005), Preface.

EDAN30610, Jun. 8, 2011.

Finney, D. J., "Graded Response: The Linear Dosage-Response Curve", Probit Analysis, 2nd Edition, Chapter 10 (1962), Cambridge Publishing Press, 16 page article.

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-Aryl-1-(4-Methylpiperazin-1-YL)Phthalazines by Suzuki-Type Cross-Coupling Reaction", Synthesis, (2001), No. 5, pp. 699-701.

Gupta, C.M., et al., "Drugs Acting on the Central Nervous System. Syntheses of Substituted Quinazolones and Quinazolines and Triazepino- and Triazocinoquinazolones", Journal of Medicinal Chemistry (1968), vol. 11, No. 2, pp. 392-395.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160.

Hayao, S., et al., "New Sedative and Hypotensive 3-Substituted 2,4(1 H,3h-)-Quinazolinediones", Journal of Medicinal Chemistry, (1965), vol. 8, pp. 807-811.

Hazard, P.R., et al., "De Quelques Actions Pharmacologiques Exercees Par Des Derives De L'Orthoprocainamide", Theérapie, (1965), vol. XX, pp. 1043-1049.

Herndon, J.L., et al., "Ketanserin Analogues: Structure-Affinity Relationships for 5-HT2 and 5-HT1C Serotonin Receptor Binding", J. Med. Chem., (1992), vol. 35, pp. 4903-4910.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 3, pp. 681-687.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 5, pp. 1286-1291.

Horvath, E.M., et al., "Poly(ADP-Ribose) Polymerase as a Drug Target for Cardiovascular Disease and Cancer: An Update", Drug News Perspect, (2007), vol. 20, No. 3, pp. 171-181.

Jordan, V.C., "Tamoxifen: A Most Unlikely Pioneering Medicine", Nature Reviews, (2003), vol. 2, pp. 205-213.

Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920.

Kormendy, K. and Ruff, F., "Aminophthalazinone Derivatives, VII* Reaction of Chlorophthalazinone With Secondary Amines Study of the Steric Effect, II.", Acta Chimica Academiae Scientiarum Hungaricae, 1981, pp. 155-166, vol. 106(2).

Kormendy, K. and Ruff, F., "Aminophthalazinone Derivatives, VII. Methods for the Synthesis of Imidazo[2,1-α]Phthalazine and Pirimido[2,1-aα]Phthalazine Ring Systems, I.", Acta Chimica Hungarica, 1983, pp. 65-82, vol. 112(1).

Kormendy, K., et al., "Aminophthalazinone Derivatives, V Synthesis of 4-Hydrazino-1-(2-H)Ophthalazinones, I", Acta Chimica Academiae Scientiarum Hungaricae, (1979), vol. 102, No. 1, pp. 39-50.

Kornet, M.J., et al., "Synthesis of 3-Amino-2,4(1H,3H)-Quinazolinediones for Testing as Anticonvulsants", J. Heterocyclic Chem., (1984), vol. 21, No. 5, pp. 1533-1535.

Kulcsar, G., et al., Synthesis and Study of New 4-Quinazolinone Inhibitors of the DNA Repair Enzyme Poly(ADP-Ribose) Polymerase (PARP), Arkivoc, XX,XX, (2003), vol. 2003, No. Part V, pp. 121-131.

Larner, A.J., "Poly(ADP-Ribose) Polymerase Inhibitors in the Prevention of Neuronal Cell Death", Expert Opin. Ther. Patents, (2002), vol. 12, No. 4, pp. 481-487.

Leysen et al., "Non-serotonergic [$^3$H]ketanserin binding sites in striatal membranes are associated with a dopac release system on dopaminergic nerve endings.", European Journal of Pharmacology, 1987, 134(3) 373-375.

Lord, C.J., et al., "Targeted Therapy for Cancer Using PARP Inhibitors", Current Opinion in Pharmacology, (2008), vol. 8, pp. 363-369.

Meier, H.L., et al., "Alterations in Human Lymphocyte DNA Caused by Sulfur Mustard Can be Mitigated by Selective Inhibitors of Poly(ADP-Ribose) Polymerase", Biochimica et Biophysica Acta, (1998), vol. 1404, pp. 367-376.

Miller, B.A., "Inhibition of TRPM2 Function by PARP Inhibitors Protects Cells From Oxidative Stress-Induced Death", British Journal of Pharmacology, (2004), vol. 143, pp. 515-516.

Nguewa, P.A., et al., "Poly(ADP-Ribose) Polymerases: Homology, Structural Domains and Functions. Novel Therapeutical Applications", Progress in Biophysics & Molecular Biology, (2005), vol. 88, pp. 143-172.

Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.

Pailer et al., "Syntheisis of quinoxalone derivatives.", Monatshefte fuer Chemie, 1962, pp. 1005-1010, vol. 93.

Patent Abstracts of Japan, vol. 1998, No. 5, Apr. 30, 1998—& JP 10007572 A (Sumitomo Pharmaceut Co Ltd), Jan. 13, 1998 '0046!, Formula 14 abstract.

Schreiber, V., et al., "Poly(ADP-Ribose) Polymerase-2 is Required for Efficient Base Excision DNA Repair in Association With PARP-1 and XRCC1", Journal of Biological Chemistry, (2002), vol. 277, No. 25, pp. 23028-23036.

Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658.

Takai, H., et al., "Synthesis of Piperidine Derivatives With a Quinazoline Ring System as Potential Antihypertensive Agents", Chem. Pharm. Bull, (1986), vol. 34, No. 5, pp. 1907-1916.

Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105.

Tentori, L., et al. "Poly(ADP-ribose)polymerase (PARP) Inhibition or PARP-1 gene Deletion Reduces Angiogenesis", European Journal of Cancer, vol. 43, No. 14 (2007) pp. 2124-2133.

Tentori, L., et al., "Chemopotentiation by PARP Inhibitors in Cancer Therapy", Pharmacological Research, (2005), vol. 52, pp. 25-33.

The Merck Index, 13th Ed., p. 670, monograph for "Ethyl Alcohol" © 2001 by Merck and Co., Inc.

Vippagunta, S.R., et al., "Crystalline Solids", Advanced Drug Delivery Reviews, (2001), vol. 48, pp. 3-26.

Virag, L., et al., "The Therapeutic Potential of Poly(ADP-Ribose) Polymerase Inhibitors", Pharmacological Reviews, (2002), vol. 54, No. 3, pp. 375-429.

Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377.

Zhang, J., "PARP Inhibition: A Novel Approach to Treat Ischaemia/Reperfusion and Inflammation-Related Injuries", Emerging Drugs, (1999), vol. 4, pp. 209-221.

International Search report for Application No. PCT/EP2004/013163 mailed Apr. 20, 2005.

International Search report for Application No. PCT/EP2004/013164 mailed Mar. 14, 2005.

International Search report for Application No. PCT/EP2004/013165 mailed Mar. 24, 2005.

International Search report for Application No. PCT/EP2005/053029 mailed Oct. 7, 2005.

International Search report for Application No. PCT/EP2005/053030 mailed Oct. 24, 2005.

International Search report for Application No. PCT/EP2005/053031 mailed Oct. 25, 2005.

International Search report for Application No. PCT/EP2008/052764 mailed Aug. 12, 2008.

International Search report for Application No. PCT/EP2008/064243 mailed Mar. 30, 2009.

International Search report for Application No. PCT/EP2009/053598 mailed May 19, 2009.

International Search report for Application No. PCT/EP2009/053604 mailed May 8, 2009.

* cited by examiner

7-PHENYLALKYL SUBSTITUTED 2-QUINOLINONES AND 2-QUINOXALINONES AS POLY(ADP-RIBOSE) POLYMERASE INHIBITORS

CROSS REFERENCE TO RELATED APPLICATIONS

This application is a Divisional of U.S. Ser. No. 10/595,882, currently pending, filed May 17, 2006, which claims priority from National Stage Application No. PCT/EP2004/013162, filed Nov. 18, 2004, which claims priority from EPO Patent Application No. 03078650.3, filed Nov. 20, 2003.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-ribose) polymerase-1 (PARP-1) is a member of the PARP enzyme family consisting of PARP-1 and several recently identified novel poly(ADP-ribosylating) enzymes. PARP is also referred to as poly(adenosine 5'-diphospho-ribose) polymerase or PARS (poly (ADP-ribose) synthetase).

PARP-1 is a major nuclear protein of 116 kDa consisting of three domains: the N-terminal DNA binding domain containing two zinc fingers, the automodification domain and the C-terminal catalytic domain. It is present in almost all eukaryotes. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{2+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold.

Among the many functions attributed to PARP, and especially PARP-1, is its major role in facilitating DNA repair by ADP-ribosylation and therefore co-ordinating a number of DNA repair proteins. As a result of PARP activation, $NAD^+$ levels significantly decline. Extensive PARP activation leads to severe depletion of $NAD^+$ in cells suffering from massive DNA damage. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^+$ depletion due to poly(ADP-ribose) turnover. Thus, PARP or PARG inhibition is expected to preserve the cellular energy level thereby potentiating the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues.

PARP is activated by damaged DNA fragments and, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of $NAD^+$ regenerated, $NAD^+$ is depleted by massive PARP activation, in the efforts to re-synthesize $NAD^+$, ATP may also become depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency. The potential role of PARP inhibitors in treating neurodegenerative diseases and head trauma has thus been recognized even if the exact mechanism of action has not yet been elucidated.

Similarly, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%) These results make it reasonable to assume that PARP inhibitors could salvage previously ischaemic heart or reperfusion injury of skeletal muscle tissue.

PARP activation can also be used as a measure of damage following neurotoxic insults resulting from exposure to any of the following inducers like glutamate (via NMDA receptor stimulation), reactive oxygen intermediates, amyloid β-protein, N-methyl-4-phenyl-1,2,3,6-tetrahydropyridine (MPTP) or its active metabolite N-methyl-4 phenylpyridine ($MPP^+$), which participate in pathological conditions such as stroke, Alzheimer's disease and Parkinson's disease. Other studies have continued to explore the role of PARP activation in cerebellar granule cells in vitro and in MPTP neurotoxicity. Excessive neural exposure to glutamate, which serves as the predominate central nervous system neurotransmitter and acts upon the N-methyl D-aspartate (NMDA) receptors and other subtype receptors, most often occurs as a result of stroke or other neurodegenerative processes. Oxygen deprived neurons release glutamate in great quantities during ischaemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro.

Another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs.

Evidence also exists that PARP inhibitors are useful for treating inflammatory bowel disorders, such as colitis. Specifically, colitis was induced in rats by intraluminal administration of the hapten trinitrobenzene sulfonic acid in 50% ethanol. Treated rats received 3-aminobenzamide, a specific inhibitor of PARP activity Inhibition of PARP activity reduced the inflammatory response and restored the morphology and the energetic status of the distal colon.

Further evidence suggests that PARP inhibitors are useful for treating arthritis. Further, PARP inhibitors appear to be useful for treating diabetes. PARP inhibitors have been shown to be useful for treating endotoxic shock or septic shock.

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence disease; and to alter gene expression of senescent cells.

It is also known that PARP inhibitors, such as 3-amino benzamide, affect overall DNA repair in response, for example, to hydrogen peroxide or ionizing radiation.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

PARP inhibitors have been used to treat cancer. In addition, U.S. Pat. No. 5,177,075 discusses several isoquinolines used for enhancing the lethal effects of ionizing radiation or chemotherapeutic agents on tumor cells. Weltin et al., "Effect of 6(5-Phenanthridinone, an Inhibitor of Poly(ADP-ribose) Polymerase, on Cultured Tumor Cells", Oncol. Res., 6:9, 399-403 (1994), discusses the inhibition of PARP activity, reduced proliferation of tumor cells, and a marked synergistic effect when tumor cells are co-treated with an alkylating drug.

A recent comprehensive review of the state of the art has been published by Li and Zhang in IDrugs 2001, 4(7): 804-812.

There continues to be a need for effective and potent PARP inhibitors, and more particularly PARP-1 inhibitors which produce minimal side effects. The present invention provides compounds, compositions for, and methods of, inhibiting PARP activity for treating cancer and/or preventing cellular, tissue and/or organ damage resulting from cell damage or death due to, for example, necrosis or apoptosis. The compounds and compositions of the present invention are especially useful in enhancing the effectiveness of chemotherapy and radiotherapy where a primary effect of the treatment is that of causing DNA damage in the targeted cells.

BACKGROUND PRIOR ART

EP 371564, published on June 6, 1990, discloses (1H-azol-1-ylmethyl) substituted quinoline, quinazoline or quinoxaline derivatives. The described compounds suppress the plasma elimination of retinoic acids. More in particular the compound 3-ethyl-7-[(1H-imidazol-1-ylphenylmethyl]-2 (1H)-quinoxalinone (compound No 19 of the present application) and the compound 7-[(4-chlorophenyl)-1H-imidazol-1-ylmethyl]-3-methyl-2(1H)-quinoxalinone (compound No 20 of the present application) were disclosed.

Compound 19

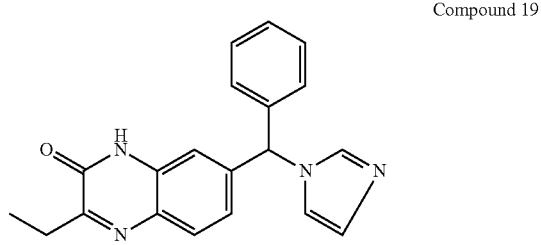

Compound 20

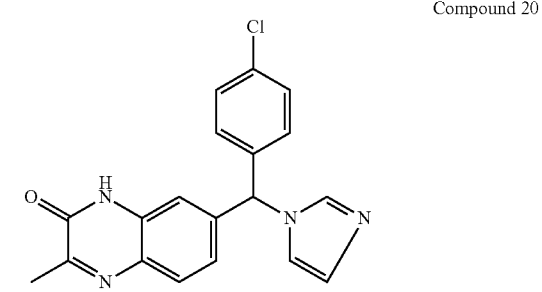

DESCRIPTION OF THE INVENTION

This invention concerns compounds of formula (I)

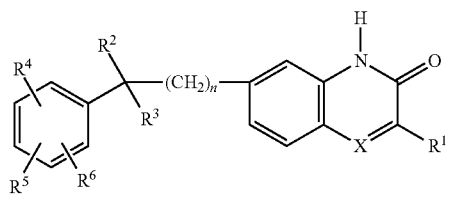
(I)

the N-oxide forms, the addition salts and the stereo-chemically isomeric forms thereof,
wherein
n is 0, 1 or 2;
X is N or $CR^7$, wherein $R^7$ is hydrogen or taken together with $R^1$ may form a bivalent radical of formula —CH=CH—CH=CH—;
$R^1$ is $C_{1-6}$alkyl or thienyl;
$R^2$ is hydrogen, hydroxy, $C_{1-6}$alkyl, $C_{3-6}$alkynyl or taken together with $R^3$ may form =O;
$R^3$ is a radical selected from —(CH$_2$)$_s$—NR$^8$R$^9$ (a-1), —O—H (a-2), —O—R$^{10}$ (a-3), —S—R$^{11}$ (a-4), or —C≡N (a-5), wherein
s is 0, 1, 2 or 3;
$R^8$ is —CHO, $C_{1-6}$alkyl, hydroxy$C_{1-6}$alkyl, $C_{1-6}$alkylcarbonyl, di($C_{1-6}$alkyl)amino$C_{1-6}$alkyl, $C_{1-6}$alkyloxy$C_{1-6}$alkyl, $C_{1-6}$alkylcarbonylamino$C_{1-6}$alkyl, piperidinyl$C_{1-6}$ alkyl, piperidinyl$C_{1-6}$alkylaminocarbonyl, $C_{1-6}$alkyloxy, thienyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl;
$R^9$ is hydrogen or $C_{1-6}$alkyl;
$R^{10}$ is $C_{1-6}$alkyl, $C_{1-6}$alkylcarbonyl or di($C_{1-6}$alkyl)amino$C_{1-6}$alkyl; and
$R^{11}$ is di($C_{1-6}$alkyl)amino$C_{1-6}$alkyl;
or $R^3$ is a group of formula —(CH$_2$)$_t$—Z— (b-1), wherein
t is 0, 1, 2 or 3;
Z is a heterocyclic ring system selected from

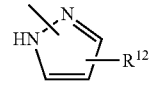
(c-1)

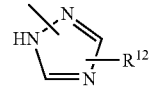
(c-2)

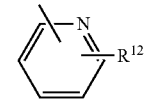
(c-3)

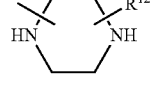
(c-4)

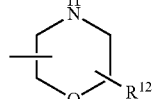
(c-5)

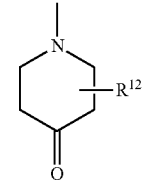
(c-6)

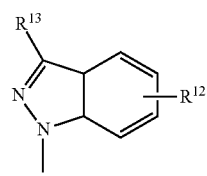
(c-7)

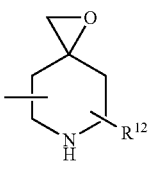
(c-8)

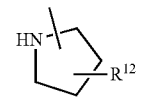
(c-9)

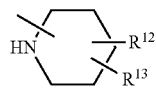
(c-10)

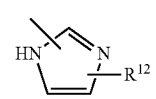
(c-11)

wherein each $R^{12}$ independently is hydrogen, $C_{1-6}$alkyl, aminocarbonyl, hydroxy,

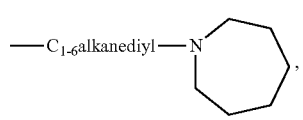

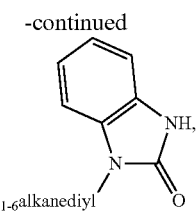
—C$_{1-6}$alkanediyl

C$_{1-6}$alkyloxyC$_{1-6}$alkyl, C$_{1-6}$alkyloxyC$_{1-6}$alkylamino, di(phenyl)C$_{1-6}$alkenyl, piperidinylC$_{1-6}$alkyl, C$_{3-10}$cycloalkyl, C$_{3-10}$cycloalkylC$_{1-6}$alkyl, aryloxy(hydroxy)C$_{1-6}$alkyl, haloindazolyl, arylC$_{1-6}$alkyl, arylC$_{2-6}$alkenyl, morpholino, C$_{1-6}$alkylimidazolyl, or pyridinylC$_{1-6}$alkylamino; and each R$^{13}$ independently is hydrogen, piperidinyl or aryl;

Alternatively, R$^{12}$ independently is hydrogen, halo, C$_{1-6}$alkyl, aminocarbonyl, amino, hydroxy, aryl,

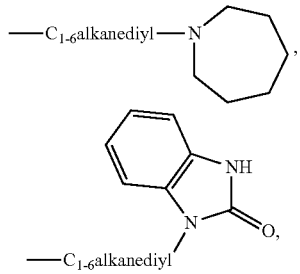
—C$_{1-6}$alkanediyl

C$_{1-6}$ alkylaminoC$_{1-6}$ alkyloxy, C$_{1-6}$ alkyloxyC$_{1-6}$ alkyl, C$_{1-6}$ alkyloxyC$_{1-6}$ alkylamino, arylC$_{1-6}$ alkyl, di(phenylC$_{2-6}$ alkenyl), piperidinyl, piperidinylC$_{1-6}$ alkyl, C$_{3-10}$ cycloalkyl, C$_{3-10}$ cycloalkylC$_{1-6}$ alkyl, aryloxy(hydroxy)C$_{1-6}$ alkyl, haloindazolyl, arylC$_{1-6}$ alkyl, arylC$_{2-6}$ alkenyl, arylC$_{1-6}$ alkylamino, morpholino, C$_{1-6}$ alkylimidazolyl, or pyridinylC$_{1-6}$ alkylamino.

R$^4$, R$^5$ and R$^6$ are each independently selected from hydrogen, halo, trihalomethyl, trihalomethoxy, C$_{1-6}$alkyl, C$_{1-6}$alkyloxy, di(C$_{1-6}$alkyl)amino, di(C$_{1-6}$alkyl)aminoC$_{1-6}$alkyloxy or C$_{1-6}$alkyloxycarbonyl; or when R$^5$ and R$^6$ are on adjacent positions they may taken together form a bivalent radical of formula —O—CH$_2$—O— (d-1), —O—(CH$_2$)$_2$—O— (d-2), —CH=CH—CH=CH— (d-3), or —NH—C(O)—NR$^{14}$=CH— (d-4), wherein R$^{14}$ is C$_{1-6}$alkyl;

aryl is phenyl or phenyl substituted with halo, C$_{1-6}$alkyl or C$_{1-6}$alkyloxy;

with the proviso that when n is 0, X is N, R$^1$ is C$_{1-6}$alkyl, R$^2$ is hydrogen, R$^3$ is a group of formula (b-1), t is 0, Z is the heterocyclic ring system (c-2) wherein said heterocyclic ring system Z is attached to the rest of the molecule with a nitrogen atom, and R$^{12}$ is hydrogen; then at least one of the substituents R$^4$, R$^5$ or R$^6$ is other than hydrogen, halo, C$_{1-6}$alkyl or C$_{1-6}$alkyloxy.

Whenever the heterocyclic ring system Z contains a —CH$_2$—, —CH=, or —NH— moiety the substituents R$^{12}$ and R$^{13}$ or the rest of the molecule can be attached to the carbon or nitrogen atom in which case one or both hydrogen atoms are replaced.

Alternatively, R$^4$, R$^5$ and R$^6$ are each independently selected from hydrogen, halo, trihalomethyl, trihalomethoxy, C$_{1-6}$alkyl, C$_{1-6}$alkyloxy, amino, aminoC$_{1-6}$alkyl, di(C$_{1-6}$ alkyl)amino, di(C$_{1-6}$alkyl)aminoC$_{1-6}$alkyloxy or C$_{1-6}$alkyloxycarbonyl, or C$_{1-6}$alkyl substituted with 1, 2 or 3 substituents independently selected from hydroxy, C$_{1-6}$alkyloxy, or aminoC$_{1-6}$alkyloxy; or when R$^5$ and R$^6$ are on adjacent positions they may taken together form a bivalent radical of formula —O—CH$_2$—O—, (d-1)

—O—(CH$_2$)$_2$—O—, (d-2)

—CH=CH—CH=CH—, or (d-3)

—NH—C(O)—NR$^{14}$=CH—. (d-4)

Alternatively, R$^8$, R$^{10}$ and R$^{11}$ are each independently selected from —CHO, C$_{1-6}$alkyl, hydroxyC$_{1-6}$alkyl, C$_{1-6}$alkylcarbonyl, amino, C$_{1-6}$ alkylamino, di(C$_{1-6}$ alkyl)aminoC$_{1-6}$alkyl, C$_{1-6}$alkyloxycarbonyl, C$_{1-6}$alkylcarbonylaminoC$_{1-6}$alkyl, piperidinylC$_{1-6}$alkylaminocarbonyl, piperidinyl, piperidinylC$_{1-6}$alkyl, piperidinylC$_{1-6}$ 6 alkylaminocarbonyl, C$_{1-6}$alkyloxy, thienylC$_{1-6}$alkyl, pyrrolylC$_{1-6}$alkyl, arylC$_{1-6}$6alkylpiperidinyl, arylcarbonylC$_{1-6}$ alkyl, arylcarbonylpiperidinylC$_{1-6}$alkyl, haloindozolylpiperidinylC$_{1-6}$alkyl, or arylC$_{1-6}$alkyl(C$_{1-6}$alkyl)aminoC$_{1-6}$ alkyl.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; C$_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; C$_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihaloC$_{1-6}$alkyl defines C$_{1-6}$alkyl containing three identical or different halo substituents for example trifluoromethyl; C$_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; C$_{3-6}$alkynyl defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; C$_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and solvates and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Whenever used hereinafter, the term "compounds of formula (I)" is meant to include also the N-oxide forms, the pharmaceutically acceptable acid or base addition salts and all stereoisomeric forms.

The compounds described in EP 371564 suppress the plasma elimination of retinoic acids. The compound 3-ethyl-7-[(1H-imidazol-1-ylphenylmethyl]-2(1H)-quinoxalinone (compound No 19 of the present application) and the compound 7-[(4-chlorophenyl)-1H-imidazol-1-ylmethyl]-3-methyl-2(1H)-quinoxalinone (compound No. 20 of the present application) have been disclosed in EP 371564. Unexpectedly, it has been found that the compounds of the present invention show PARP inhibitory activity.

A first group of interesting compounds consists of those compounds of formula (I) wherein one or more of the following restrictions apply:

a) n is 0 or 1;
b) X is N or $CR^7$, wherein $R^7$ is hydrogen;
c) $R^1$ is $C_{1-6}$alkyl;
d) $R^2$ is hydrogen;
e) $R^3$ is a radical selected from (a-1) or (a-2) or is group of formula (b-1);
f) s is 0, 1 or 2;
g) $R^8$ is $C_{1-6}$alkyl or aryl$C_{1-6}$alkyl($C_{1-6}$alkyl)amino$C_{1-6}$alkyl;
h) t is 0, 1 or 2;
i) Z is a heterocyclic ring system selected from (c-1), (c-2), (c-3), (c-4), (c-5) or (c-11);
j) each $R^{12}$ independently is hydrogen or $C_{1-6}$alkyloxy$C_{1-6}$alkylamino;
k) each $R^{13}$ independently is hydrogen; and
l) $R^4$, $R^5$ and $R^6$ are each independently selected from hydrogen, halo or $C_{1-6}$alkyl.

A second group of interesting compounds consists of those compounds of formula (I) wherein one or more of the following restrictions apply:

a) n is 0 or 1;
b) X is N;
c) $R^1$ is $C_{1-6}$alkyl;
d) $R^2$ is hydrogen
e) $R^3$ is a radical of formula (a-1) or is a group of formula (b-1);
f) s is 0;
g) $R^8$ is aryl$C_{1-6}$alkyl($C_{1-6}$alkyl)amino$C_{1-6}$alkyl;
h) t is 0;
i) Z is a heterocyclic ring system selected from (c-1) or (c-2);
j) each $R^{12}$ independently is hydrogen or $C_{1-6}$alkyloxy$C_{1-6}$alkylamino;
k) each $R^{13}$ independently is hydrogen; and
k) $R^4$, $R^5$ and $R^6$ are each independently selected from hydrogen or halo.

A third group of interesting compounds consists of those compounds of formula (I), the first group of interesting compounds or the second group of interesting compounds wherein Z is a heterocyclic ring system other than the heterocyclic ring system of formula (c-2) or (c-4).

A group of preferred compounds consists of those compounds of formula (I) wherein n is 0 or 1; X is N or $CR^7$, wherein $R^7$ is hydrogen; $R^1$ is $C_{1-6}$alkyl; $R^2$ is hydrogen; $R^3$ is a radical selected from (a-1) or (a-2) or is group of formula (b-1); s is 0, 1 or 2; $R^8$ is $C_{1-6}$alkyl or aryl$C_{1-6}$alkyl ($C_{1-6}$alkyl)amino$C_{1-6}$alkyl; t is 0, 1 or 2; Z is a heterocyclic ring system selected from (c-1), (c-2), (c-3), (c-4), (c-5) or (c-1 1); each $R^{12}$ independently is hydrogen or $C_{1-6}$alkyloxy$C_{1-6}$alkylamino; each $R^{13}$ independently is hydrogen; and $R^4$, $R^5$ and $R^6$ are each independently selected from hydrogen, halo or $C_{1-6}$alkyl.

A further group of preferred compounds consists of those compounds of formula (I) wherein n is 0 or 1; X is N; $R^1$ is $C_{1-6}$alkyl; $R^2$ is hydrogen; $R^3$ is a radical of formula (a-1) or is a group of formula (b-1); s is 0; $R^8$ is aryl$C_{1-6}$alkyl($C_{1-6}$alkyl)amino$C_{1-6}$alkyl; t is 0; Z is a heterocyclic ring system selected from (c-1) or (c-2); each $R^{12}$ independently is hydrogen or $C_{1-6}$alkyloxy$C_{1-6}$alkylamino; each $R^{13}$ independently is hydrogen; and $R^4$, $R^5$ and $R^6$ are each independently selected from hydrogen or halo.

An even further group of preferred compounds consists of those compounds of formula (I), the group of preferred compounds or the further group of preferred compounds wherein Z is a heterocyclic ring system other than the heterocyclic ring system of formula (c-2) or (c-4).

The most preferred compounds are compound No 5, compound No 9, compound No 2 and compound No 1.

compound 5

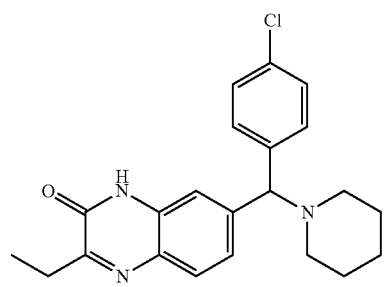

compound 9

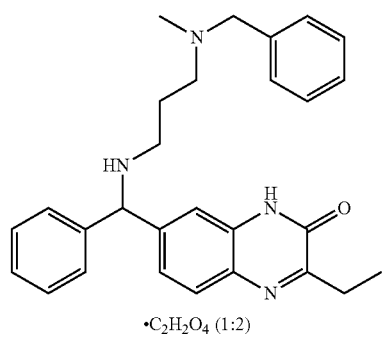
·$C_2H_2O_4$ (1:2)

compound 2

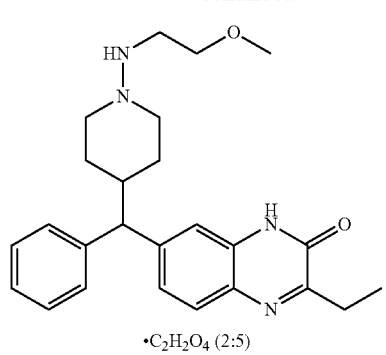
·$C_2H_2O_4$ (2:5)

compound 1

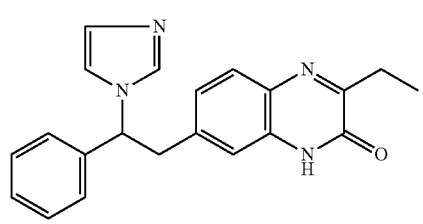

The compounds of formula (I) can be prepared according to the general methods described in EP 371564.

A number of such preparation methods will be described hereinafter in more detail. Other methods for obtaining final compounds of formula (I) are described in the examples.

Compounds of formula (I) wherein $R^2$ is hydrogen and $R^3$ is —$NR^9$—CHO wherein $R^9$ is hydrogen or methyl, herein referred to as compounds of formula (I-b), can be prepared starting from compounds of formula (I), wherein $R^2$ taken together with $R^3$ forms =O, herein referred to as compounds of formula (I-a), in the presence of formamide or methylformamide, here indicated as intermediates of formula (II), and formic acid.

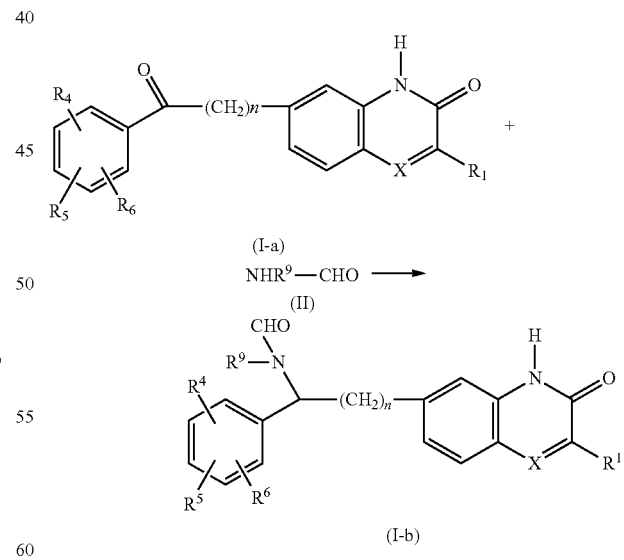

Compounds of formula (I), wherein $R^3$ is hydroxy, herein referred to as compounds of formula (I-c), can be prepared by converting the keton moiety of compounds of formula (I-a) into an hydroxy group, with an appropriate reductant, e.g., sodium borohydride in a suitable solvent, e.g. methanol and tetrahydrofuran.

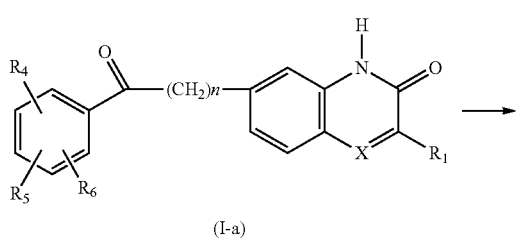

(I-a)

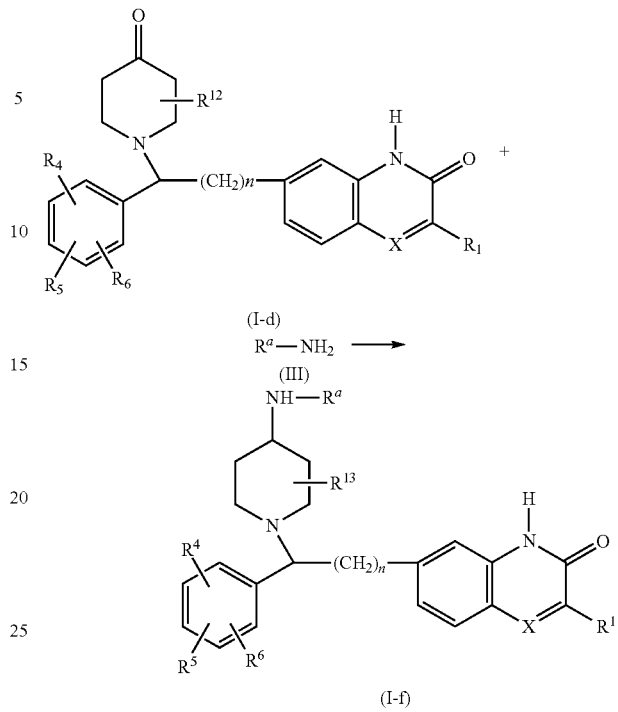

(I-c)

Compounds of formula (I-a) can be prepared by converting compounds of formula (I-c), wherein $R^2$ is hydrogen, herein referred to as compounds of formula (I-c-1), in the presence of a suitable oxidant such as chromium trioxide and an acid such as sulfuric acid, in a suitable solvent such as 2-propanone.

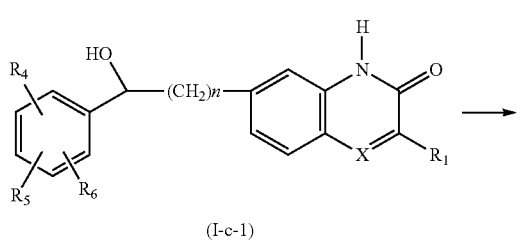

(I-c-1)

(I-a)

Compounds of formula (I) wherein $R^2$ is hydrogen and $R^3$ is a radical of formula (c-1), herein referred to as a compound of formula (I-f), can be prepared by reacting compounds of formula (I) wherein $R^2$ is hydrogen and $R^3$ is a radical of formula (c-8), herein referred to as compounds of formula (I-d), with an amine of formula (III), wherein $R^a$ is an appropriate radical, in the presence of a suitable solvent such as methanol and a suitable reagent such as sodium cyanoborohydride.

Intermediates of formula (IV), wherein W is an appropriate leaving group such as, for example, chloro, bromo, methanesulfonyloxy or benzenesulfonyloxy can be prepared from compounds of formula (I-c-1) by treating said compounds with a suitable reagent e.g. methanesulfonyloxy chloride or benzenesulfonyloxy chloride, or a halogenating reagent such as e.g. $POCl_3$ or $SOCl_2$.

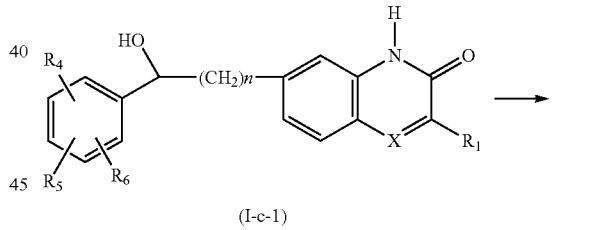

(I-c-1)

(IV)

Compounds of formula (I), defined as compounds of formula (I) wherein $R^b$ is as defined in $R^8$ and $R^c$ is as defined in $R^9$, or $R^b$ and $R^c$ taken together with the nitrogen to which they are attached, form an appropriate heterocyclic ring system as defined in Z, herein referred to as compounds of formula (I-h), can be prepared by reacting an intermediate of formula (IV) with an intermediate of formula (V). The reaction can be performed in a reaction-inert solvent such as dimethylformamide or acetonitrile, and optionally in the presence of a suitable base such as, for example, sodium carbonate, potassium carbonate or thriethylamine

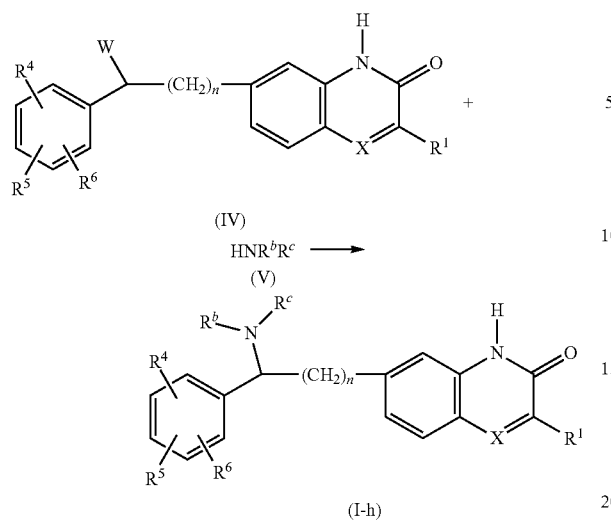

(IV)

HNR$^b$R$^c$ (V)

(I-h)

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

Hence, compounds of formula (I), (I-a), (I-b), (I-c), (I-c-1), (I-d), (I-e), (I-f), (I-h), (I-i), (I-j) and (I-k) can optionally be the subject of one or more of the following conversions in any desired order:

(i) converting a compound of formula (I) into a different compound of formula (I);

(ii) converting a compound of formula (I) into the corresponding acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

Intermediates of formula (VII), wherein R$^d$ and R$^e$ are appropriate radicals or taken together with the carbon to which they are attached, form an appropriate heterocyclic ring system as defined in Z, can be prepared by hydrolysing intermediates of formula (VI), wherein R$^3$ is a group of formula (b-1) or a radical of formula (a-1) wherein s is other than 0, herein referred to as R$^g$, according to art-known methods, such as stirring the intermediate (VI) in an aqueous acid solution in the presence of a reaction inert solvent, e.g. tetrahydrofuran. An appropriate acid is for instance hydrochloric acid.

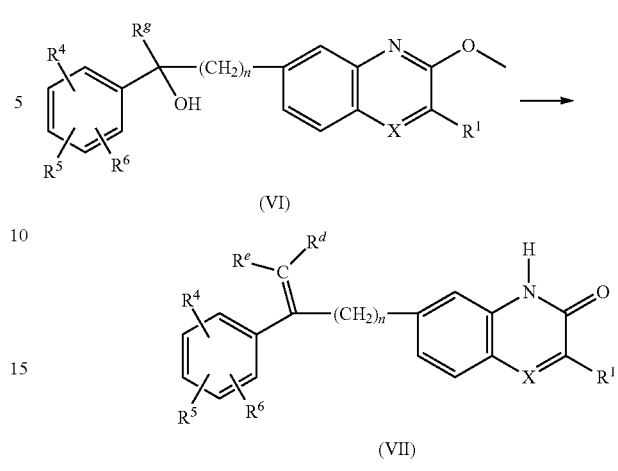

(VI)

(VII)

Compounds of formula (I) wherein R$^2$ is hydrogen and R$^8$ is as defined above, herein referred to as compounds of formula (I-k), can be prepared starting from intermediates of formula (VII), by a selective hydrogenation of said intermediate with an appropriate reducing agent such as, for example with a noble catalyst, such as platinum-on-charcoal, palladium-on-charcoal and the like and an appropriate reductant such as hydrogen in a suitable solvent such as methanol.

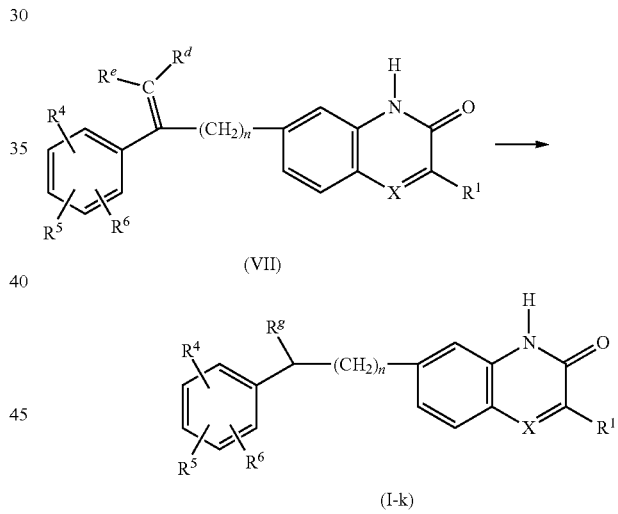

(VII)

(I-k)

Compounds of formula (I) can be prepared by hydrolysing intermediates of formula (VIII), according to art-known methods, by submitting the intermediates of formula (VIII) to appropriate reagents, such as, tinchloride, acetic acid and hydrochloric acid, in the presence of a reaction inert solvent, e.g. tetrahydrofuran.

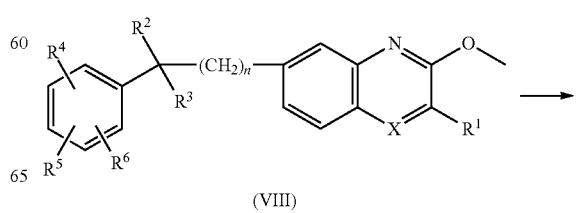

(VIII)

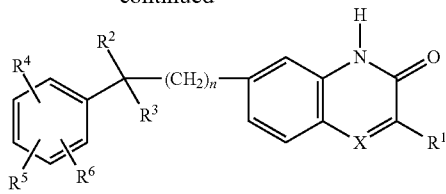

(I)

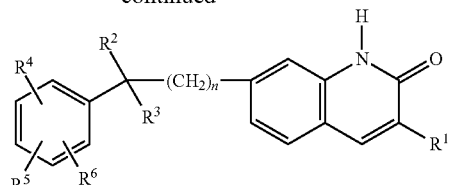

(I-j)

Compounds of formula (I) can be prepared starting from N-oxides of formula (IX) by converting the intermediates of formula (IX) in the presence of a suitable reagent such as sodium carbonate or acetic anhydride and when appropriate in a solvent such as dichloromethane.

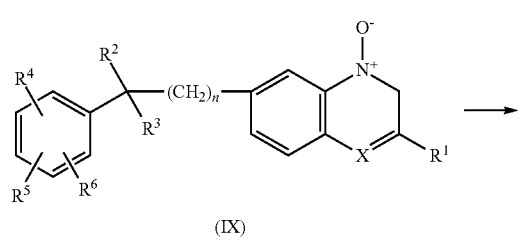

(IX)

↓

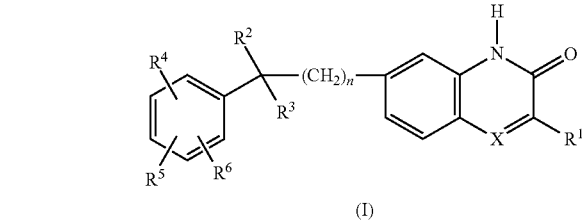

(I)

The compounds of formula (I) wherein X is CH herein referred to as compounds of formula (I-j), may also be obtained by cyclizing an intermediate of formula (X). The cyclization reaction of intermediates of formula (X) may be conducted according to art-known cyclizing procedures. Preferably the reaction is carried out in the presence of a suitable Lewis Acid, e.g. aluminum chloride either neat or in a suitable solvent such as, for example, an aromatic hydrocarbon, e.g. benzene, chlorobenzene, methylbenzene and the like; halogenated hydrocarbons, e.g. trichloromethane, tetrachloromethane and the like; an ether, e.g. tetrahydrofuran, 1,4-dioxane and the like; or mixtures of such solvents. Somewhat elevated temperatures, preferably between 70°-100° C., and stirring may enhance the rate of the reaction.

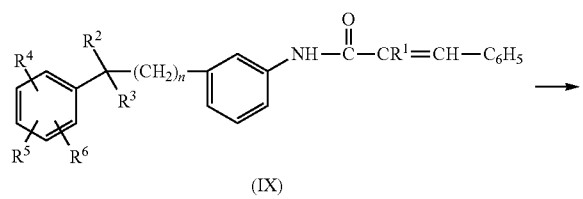

(IX)

The compounds of formula (I), wherein X is N, herein referred to as compounds of formula (I-i) may be obtained by condensing an appropriate ortho-benzenediamine of formula (XI) with an ester of formula (XII) wherein $R^h$ is $C_{1-6}$alkyl. The condensation of the substituted ortho-diamine of formula (XI) and the ester of formula (XII) can be carried out in the presence of a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like. Somewhat elevated temperatures may be appropriate to enhance the rate of the reaction and in some cases the reaction may even be carried out at the reflux temperature of the reaction mixture. The water which is liberated during the condensation may be removed from the mixture by azeotropical distillation, distillation and the like methods.

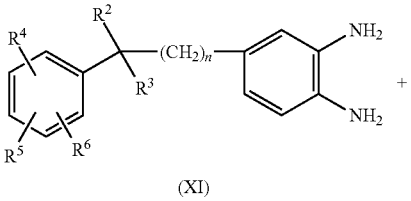

(XI)

+

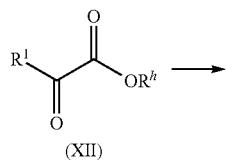

(XII)

↓

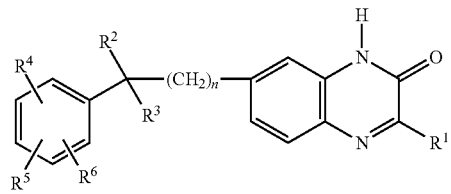

(I-i)

Intermediates of formula (XI) can be prepared by a nitro to amine reduction reaction starting with an intermediate of formula (XIII) in the presence of a metal catalyst such as Raney Nickel and an appropriate reductant such as hydrogen in a suitable solvent such as methanol.

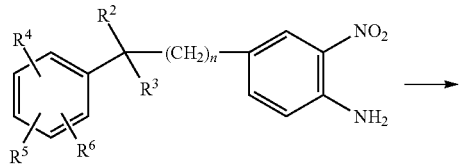

(XIII)

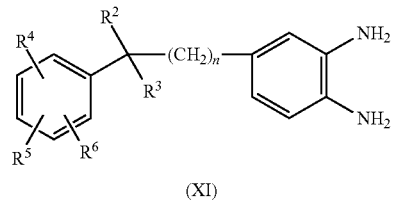

(XI)

Intermediates of formula (XIII) can be prepared by hydrolysing intermediates of formula (XIV), according to art-known methods, such as stirring the intermediate (XIV) in an aqueous acid solution in the presence of a reaction inert solvent, e.g. tetrahydrofuran,. An appropriate acid is for instance hydrochloric acid.

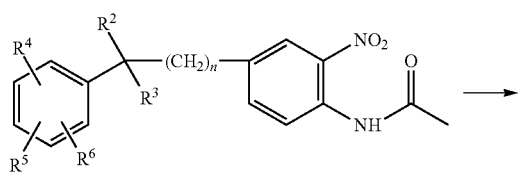

(XIII)

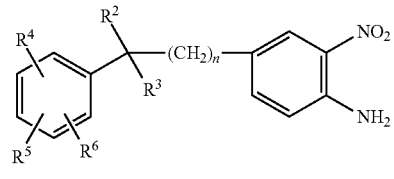

(XIII)

Intermediates of formula (X) can conveniently be prepared by reacting an aniline of formula (XV) with a halide of formula (XVI) in the presence of a base such as pyridine in a suitable solvent such as dichloromethane.

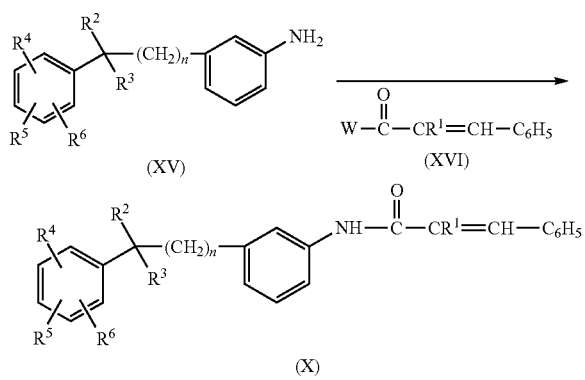

Intermediates of formula (VIII) wherein n is 0, $R^2$ is hydrogen or hydroxy and when $R^2$ is hydrogen then $R^3$ is hydroxy herein referred to as intermediates of formula (VIII-a) can be prepared by treating an intermediate of formula (XVII), wherein W is halo, with an organolithium reagent such as, e.g. n-butyllithium in a reaction inert solvent, e.g. tetrahydrofuran, and subsequently reacting said intermediate with an intermediate of formula (XVIII) wherein $R^i$ is hydrogen or a radical as defined in $R^3$.

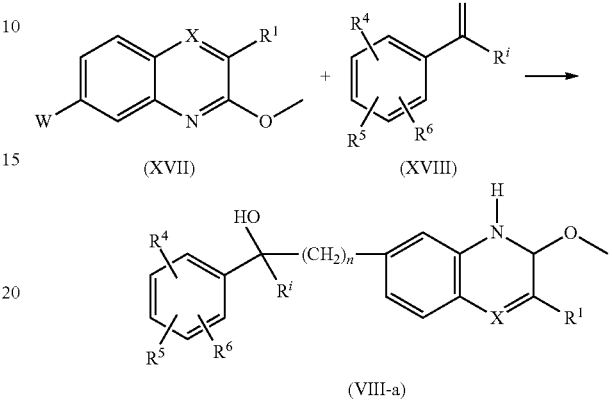

(VIII-a)

The present invention also relates to a compound of formula (I) as defined above for use as a medicine.

The compounds of the present invention have PARP inhibiting properties as can be seen from the experimental part hereinunder.

The present invention contemplates the use of compounds in the preparation of a medicament for the treatment of any of the diseases and disorders in an animal described herein, wherein said compounds are compounds of formula (I)

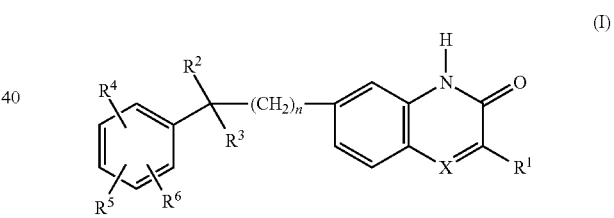

(I)

the N-oxide forms, the pharmaceutically acceptable addition salts and the stereo-chemically isomeric forms thereof, wherein n is 0, 1 or 2;

X is N or $CR^7$, wherein $R^7$ is hydrogen or taken together with $R^1$ may form a bivalent radical of formula —CH=CH—CH=CH—;

$R^1$ is $C_{1-6}$alkyl or thienyl;

$R^2$ is hydrogen, hydroxy, $C_{1-6}$alkyl, $C_{3-6}$alkynyl or taken together with $R^3$ may form =O;

$R^3$ is a radical selected from

—(CH$_2$)$_s$—NR$^8$R$^9$ (a-1),

—O—H (a-2),

—O—R$^{10}$ (a-3),

—S—R$^{11}$ (a-4), or

—C≡N (a-5), wherein s is 0, 1, 2 or 3;

$R^8$ is —CHO, $C_{1-6}$alkyl, hydroxy$C_{1-6}$alkyl, $C_{1-6}$alkylcarbonyl, di($C_{1-6}$alkyl)amino$C_{1-6}$alkyl, $C_{1-6}$alkyloxy$C_{1-6}$alkyl, $C_{1-6}$alkylcarbonylamino$C_{1-6}$alkyl, piperidinyl$C_{1-6}$ alkyl, piperidinyl$C_{1-6}$alkylaminocarbonyl, $C_{1-6}$alkyloxy, thienyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl;

$R^9$ is hydrogen or $C_{1-6}$alkyl;

$R^{10}$ is $C_{1-6}$alkyl, $C_{1-6}$alkylcarbonyl or di($C_{1-6}$alkyl)amino$C_{1-6}$alkyl; and $R^{11}$ is di($C_{1-6}$alkyl)amino$C_{1-6}$alkyl;

or $R^3$ is a group of formula $$—(CH_2)_t—Z— \quad (b-1),$$

wherein t is 0, 1, 2 or 3;

Z is a heterocyclic ring system selected from

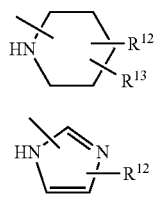 (c-1)

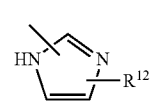 (c-2)

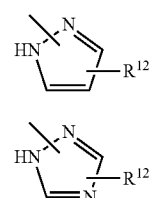 (c-3)

(c-4)

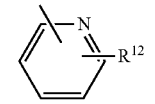 (c-5)

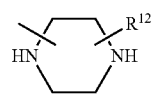 (c-6)

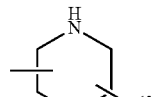 (c-7)

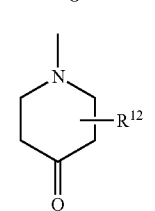 (c-8)

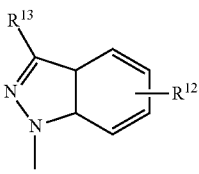 (c-9)

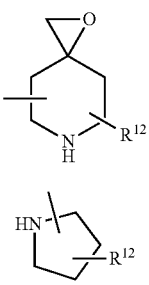 (c-10)

(c-11)

wherein each $R^{12}$ independently is hydrogen, $C_{1-6}$alkyl, aminocarbonyl, hydroxy,

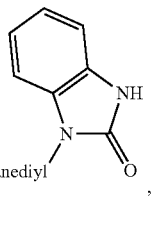

$C_{1-6}$alkyloxy$C_{1-6}$alkyl, $C_{1-6}$alkyloxy$C_{1-6}$alkylamino, di(phenyl$C_{2-6}$alkenyl), piperidinyl$C_{1-6}$alkyl, $C_{3-10}$cycloalkyl, $C_{3-10}$cycloalkyl$C_{1-6}$alkyl, aryloxy(hydroxy)$C_{1-6}$alkyl, haloindazolyl, aryl$C_{1-6}$alkyl, aryl$C_{2-6}$alkenyl, morpholino, $C_{1-6}$alkylimidazolyl, or pyridinyl$C_{1-6}$alkylamino; and each $R^{13}$ independently is hydrogen, piperidinyl or aryl;

$R^4$, $R^5$ and $R^6$ are each independently selected from hydrogen, halo, trihalomethyl, trihalomethoxy, $C_{1-6}$alkyl, $C_{1-6}$alkyloxy, di($C_{1-6}$alkyl)amino, di($C_{1-6}$alkyl)amino$C_{1-6}$ or $C_{1-6}$alkyloxycarbonyl; or when $R^5$ and $R^6$ are on adjacent positions they may taken together form a bivalent radical of formula $$—O—CH_2—O— \quad (d-1),$$

$$—O—(CH_2)_2—O— \quad (d-2),$$

$$—CH=CH—CH=CH— \quad (d-3), or$$

$$—NH—C(O)—NR^{14}=CH— \quad (d-4),$$

wherein $R^{14}$ is $C_{1-6}$alkyl;

aryl is phenyl or phenyl substituted with halo, $C_{1-6}$alkyl or $C_{1-6}$alkyloxy.

The present invention also contemplates the use of compounds of formula (I) in the preparation of a medicament for the treatment of one or more diseases and disorders in an animal described herein, wherein the compound is a compound of formula (I-1)

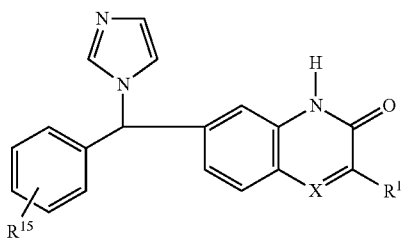

(I-1)

the N-oxide forms, the pharmaceutically acceptable addition salts and the stereo-chemically isomeric forms thereof, wherein n is 0;
X is N;
$R^1$ is methyl or ethyl;
$R^2$ is hydrogen;
$R^3$ is a group of formula (b-1);
t is 0;
—Z is the heterocyclic ring system (c-2) wherein said heterocyclic ring system —Z is attached to the rest of the molecule with a nitrogen atom;
$R^{12}$ is hydrogen; and
$R^{15}$ is hydrogen, halo, $C_{1-6}$alkyl or $C_{1-6}$alkyloxy.

More in particular the compound of formula (I-1) is 3-ethyl-7-[(1H-imidazol-1-ylphenylmethyl]-2(1H)-quinoxalinone (compound No. 19 of the present application) or 7-[(4-chlorophenyl)-1H-imidazol-1-ylmethyl]-3-methyl-2 (1H)-quinoxalinone (compound No 20 of the present application).

In view of their PARP binding properties the compounds of the present invention may be used as reference compounds or tracer compounds in which case one of the atoms of the molecule may be replaced with, for instance, a radioactive isotope.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; chemosensitize and/or radiosensitize (hypoxic) tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) for inhibiting PARD activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tumors and cancerous cells. Chemotherapy treatment of other diseases not listed herein are also contemplated by the present invention.

The compounds, compositions and methods of the present invention are particularly useful for treating or preventing tissue damage resulting from cell death or damage due to necrosis or apoptosis.

The compounds of the present invention can be "anti-cancer agents", which term also encompasses "anti-tumor cell growth agents" and "anti-neoplastic agents". For example, the methods of the invention are useful for treating cancers and chemosensitizing and/or radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma gallbladder cancer, hairy cell leukemia, head &neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva and Wilm's tumor.

Hence the compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemothearpeutic agents which act on the tumor or other therapueutically effective compounds for treating cancer or other disease.

Examples of additional therapeutical agents that may be used in conjunction with chemosensitizers include, but are not limited to: methylating agents, toposisomerase I inhibitors and other chemothearpeutic agents such as cisplatin and bleomycin.

The compounds of formula (I) can also be used to detect or identify the PARP, and more in particular the PARP-1 receptor. For that purpose the compounds of formula (I) can be labeled. Said label can be selected from the group consisting of a radioisotope, spin label, antigen label, enzyme label fluorescent group or a chemiluminiscent group.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples illustrate the present invention.

EXPERIMENTAL PART

Hereinafter, "BuLi" is defines as butyl-lithium, "MeOH" is defined as methanol,

"DIPE" is defined as diisopropyl ether, "DMF" is defined as N,N-dimethylformamide, "DME" is defined as 1,2-dimethoxyethane, "DCM" is defined as dichloromethane, "EtOAc" is defined as ethyl acetate, "THF" is defined as tetrahydrofuran, "MEK" is defined as methyl ethyl keton.

A. Preparation of the Intermediate Compounds

Example A1 a) Preparation of Intermediate 1

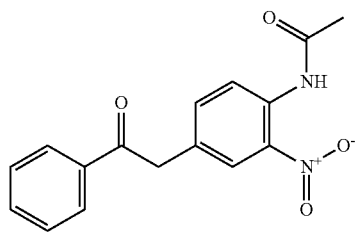 [SMILES: CC(=O)Nc1ccc(CC(=O)c2ccccc2)cc1[N+](=O)[O-]]

Nitric acid (fuming) (26.7 ml) was added dropwise at room temperature to a solution of N-[4-(2-oxo-2-phenylethyl)phenyl]-acetamide (0.2128 mol) in acetic acid, anhydride (1100 ml) while the temperature was kept below 30° C. The mixture was stirred for 1 hour, poured out into ice water and neutralized with a concentrated $NH_4OH$ solution. The precipitate was filtered off, washed with water and with diethyl ether and dried, yielding 40g (63%) of intermediate 1.

b) Preparation of Intermediate 2

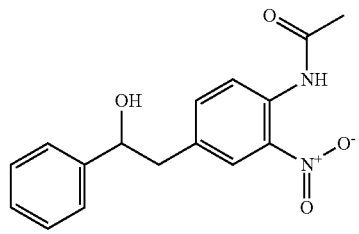 [SMILES: CC(=O)Nc1ccc(CC(O)c2ccccc2)cc1[N+](=O)[O-]]

Sodium hydroborate (0.1056 mol) was added portionwise at 10° C. under $N_2$ flow to a solution of intermediate 1 (0.096 mol) in methanol (350 ml). The mixture was stirred at 10° C. for 30 min, poured out into ice water and extracted with DCM. The organic layer was separated, dried ($MgSO_4$), filtered and the solvent was evaporated till dryness, yielding 22g (76%) of intermediate 2.

c) Preparation of Intermediate 3

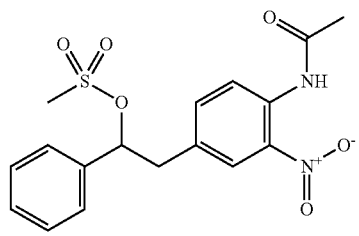 [SMILES: CC(=O)Nc1ccc(CC(OS(C)(=O)=O)c2ccccc2)cc1[N+](=O)[O-]]

Methylsulfonyl chloride (0.076 mol) was added dropwise at 0° C. under $N_2$ flow to a suspension of intermedite 2 (0.038 mol) and triethylamine (0.076 mol) in DCM (100 ml). The mixture was stirred for 12 hours. The solvent was evaporated (without heating). The product was used without further purification, yielding (quant.) of intermediate 3.

d) Preparation of intermediate 4

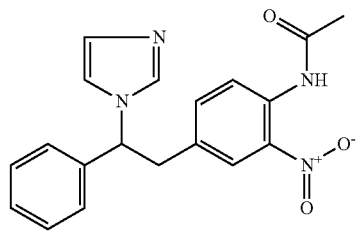 [SMILES: CC(=O)Nc1ccc(CC(c2ccccc2)n2ccnc2)cc1[N+](=O)[O-]]

A mixture of intermediate 3 (0.038 mol), 1H-imidazole (0.076 mol) and potassium carbonate (0.076 mol) in acetonitrile (300 ml) was stirred and refluxed for 15 hours, then cooled to room temperature, poured out into ice water and extracted with DCM. The organic layer was separated, dried ($MgSO_4$), filtered and the solvent was evaporated till dryness. The residue was purified by column chromatography over silica gel (eluent: $DCM/CH_3OH/NH_4OH$ 95/5/0.1). The pure fractions were collected and the solvent was evaporated, yielding 4.5g (34%) of intermediate 4.

e) Preparation of Intermediate 5

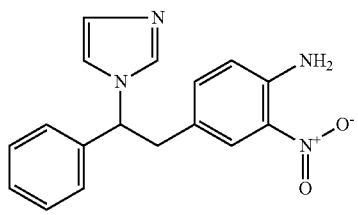 [SMILES: Nc1ccc(CC(c2ccccc2)n2ccnc2)cc1[N+](=O)[O-]]

A mixture of intermediate 4 (0.0128 mol) in sodium hydroxide (110 ml) and ethanol (30 ml) was stirred at room temperature for 3 hours, poured out on ice and extracted with DCM. The organic layer was separated, dried (MgSO₄), filtered and the solvent was evaporated till dryness, yielding 2.75g (70%) of intermediate 5.

f) Preparation of Intermediate 6

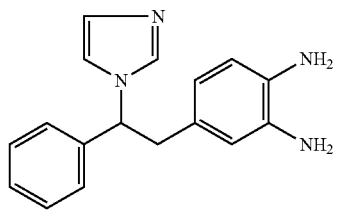 [SMILES: Nc1ccc(CC(c2ccccc2)n2ccnc2)cc1N]

A mixture of intermediate 5 (0.0089 mol) in methanol (150 ml) was hydrogenated under a 3 bar pressure for 45 min with Raney Nickel (3g) as a catalyst. After uptake of H₂ (3 equiv), the catalyst was filtered through celite and the filtrate was evaporated till dryness, yielding 2.59g (100%) of intermediate 6.

Example A2 a) Preparation of intermediate 7

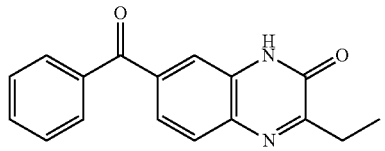 [SMILES: CCc1nc2ccc(C(=O)c3ccccc3)cc2[nH]c1=O]

A mixture of 3,4-benzophenonediamine (0.1743 mol) and ethyl-2oxobutanoate (0.3486 mol) in ethanol (820 ml) was stirred and refluxed for 5 hours and then cooled. The solvent was evaporated. The residue was taken up in an aqueous saturated NaHCO₃ solution. The mixture was extracted with DCM. The organic layer was separated, dried (MgSO₄), filtered and the solvent was evaporated till dryness. The residue (70.3 g) was purified by column chromatography over silica gel (eluent: DCM/2-propanol 98/2; 20-45 5 m). The pure fractions were collected and the solvent was evaporated, yielding 15.5 g of intermediate 7. Part of it was crystallized from diethyl ether and petroleum ether. The precipitate was filtered off and dried, yielding 0.85 g of intermediate 7, melting point 197° C.

b) Preparation of Intermediate 8

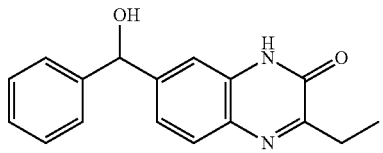 [SMILES: CCc1nc2ccc(C(O)c3ccccc3)cc2[nH]c1=O]

Sodium hydroborate (0.0719 mol) was added at 0° C. under N₂ flow to a suspension of intermediate 7 ((0.0719 mol in methanol (300 ml) and THF (100 ml). The mixture was stirred for 30 min and poured out into ice water. The precipitate was filtered off, washed with water and dried. A part (0.7 g) of this fraction (8.33 g) was crystallized from methanol and water. The precipitate was filtered off and dried, yielding 0.59 g of intermediate 8, melting point 202° C.

c) Preparation of Intermediate 9

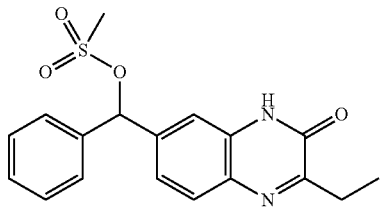 [SMILES: CCc1nc2ccc(C(OS(C)(=O)=O)c3ccccc3)cc2[nH]c1=O]

Methanesulfonyl chloride (0.009421 mol) was added at 0° C. under N₂ flow to a suspension of intermediate 8 (0.0043 mol) and triethylamine (0.0108 mol) in DCM (10 ml) and THF (10 ml). The mixture was stirred at room temperature for 5 hours. The solvent was evaporated cold. The product was used without further purification, yielding (100%) of intermediate 9.

d) Preparation of Intermediate 10

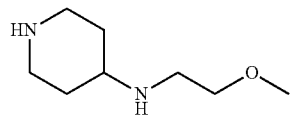

A mixture of N-(2-methoxyethyl)-1-(phenylmethyl)-4-piperidinamine (0.0402 mol) in ethanol (100 ml) was hydrogenated at 40-C for 2 hours and then at room temperature under a 3 bar pressure for 3 hours with Pd/C 10% (1 g) as a catalyst. After uptake of H₂ (1 equiv), the catalyst was filtered through celite, washed with ethanol and the filtrate was evaporated. The product was used without further purification, yielding 6.5g (99%) of intermediate 10.

Example A3 a) Preparation of Intermediate 11

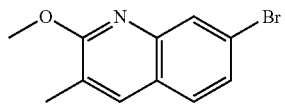

A mixture of 6-bromo-2-chloro-3-methyl-quinoline (0.0697 mol) and NaOCH₃ 30% (0.3483 mol) in methanol (90 ml) was stirred and refluxed for 15 hours. The mixture was cooled, poured out into ice water and extracted with DCM. The organic layer was separated, dried (MgSO₄), filtered and the solvent was evaporated till dryness. The product was used without further purification, yielding 12.2g (69%) of intermediate 11.

b) Preparation of Intermediate 12

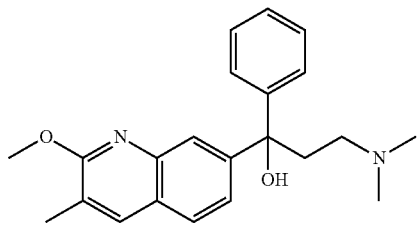

n-BuLi (0.0624 mol) was added dropwise at −60° C. under N₂ flow to a solution of intermediate 11 (0.048 mol) in THF (100 ml) and the mixture was stirred at −60° C. for 1 hour. A solution of 2-benzoylethyldimethylamine (0.0576 mol) in THF (100 ml) was added dropwise. The mixture was allowed to warm to −20° C. while stirring and then stirred for 2 hours. The mixture was poured out into an aqueous NH₄Cl solution and extracted with EtOAc. The organic layer was separated, dried (MgSO₄), filtered and the solvent was evaporated till dryness. The product was used without further purification, yielding 17.68g (quant.) of intermediate 12.

c) Preparation of Intermediate 13

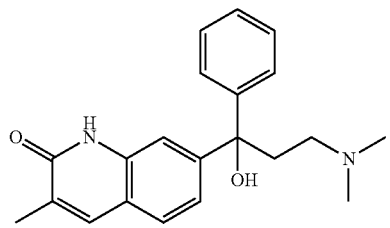 [SMILES: Cc1cc2ccc(C(O)(CCN(C)C)c3ccccc3)cc2[nH]c1=O]

A mixture of intermediate 12 (0.0496 mol) in HCl 3N (261 ml) and THF (133 ml) was stirred and refluxed for 8 hours. The mixture was cooled, poured out on ice, basified with a concentrated NH₄OH solution and extracted with DCM. The organic layer was separated, dried (MgSO₄), filtered and the solvent was evaporated till dryness. The residue was purified by column chromatography over silica gel (15-40 μm) (eluent: DCM/CH₃OH/NH₄OH 95/5/1). The pure fractions were collected and the solvent was evaporated, yielding 6g (36%) of intermediate 13.

d) Preparation of Intermediate 14

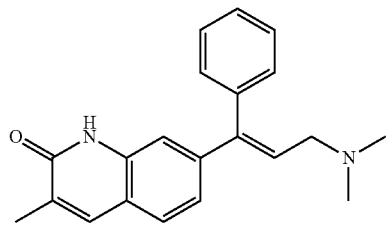 [SMILES: Cc1cc2ccc(/C(=C/CN(C)C)c3ccccc3)cc2[nH]c1=O]

A mixture of intermediate 13 (0.0178 mol) in HCl 3N (90 ml) and THF (47 ml) was stirred and refluxed for 2 days. The mixture was cooled, poured out on ice, basified with a concentrated NH₄OH solution and extracted with DCM. The organic layer was separated, dried (MgSO₄), filtered and the solvent was evaporated till dryness. The residue was crystallized from diethyl ether. The precipitate was filtered off and dried, yielding 1.5g of intermediate 14.

Example A4 a) Preparation of Intermediate 15

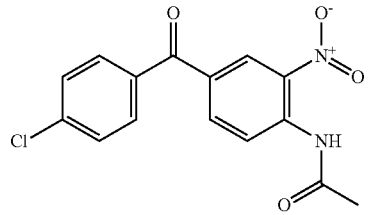 [SMILES: CC(=O)Nc1ccc(C(=O)c2ccc(Cl)cc2)cc1[N+](=O)[O-]]

A mixture of (4-amino-3-nitrophenyl)(4-chlorophenyl)-methanone (0.0686 mol) in DCM (200 ml) and acetyl chloride (20 ml) was stirred for 12 hours at room temperature and then the solvent was evaporated dry. The residue was taken up in diethyl ether (50 ml), then the desired product was filtered off and dried, yielding 21.6 g (99%) of intermediate 15, melting point 138° C.

b) Preparation of Intermediate 16

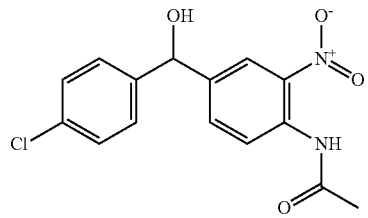 [SMILES: CC(=O)Nc1ccc(C(O)c2ccc(Cl)cc2)cc1[N+](=O)[O-]]

A mixture of intermediate 15 (0.066 mol) in methanol (200 ml) was stirred at 0° C. and a solution of sodium hydroborate (0.066 mol) in water was added dropwise, then the reaction mixture was stirred for 1 hour at room temperature and the solvent was evaporated. The residue was extracted with DCM/CH₃OH/H₂O and the extract was dried (MgSO₄). Finally the solvent was evaporated and the desired product was collected, yielding 20.4 g (97%) of intermediate 16, melting point 198° C.

c) Preparation of Intermediate 17

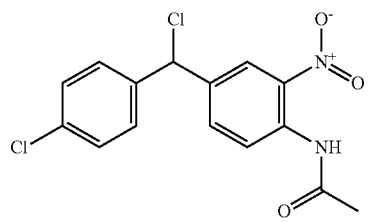 [SMILES: CC(=O)Nc1ccc(C(Cl)c2ccc(Cl)cc2)cc1[N+](=O)[O-]]

In a 3-neck reaction flask (500 ml), equipped with an addition funnel and thermometer, a mixture of intermediate 16 (0.062 mol) and triethylamine (0.125 mol) in DCM (200 ml) was cooled to 0° C. and methanesulfonyl chloride (0.125 mol) was added dropwise keeping the temperature at 0-5° C., then the reaction mixture was stirred for 4 hours at room temperature and poured out into water (1000 ml). The organic layer was separated, dried (MgSO$_4$), filtered off and the solvent was evaporated, yielding 18 g (oil, 85%) of intermediate 17.

d) Preparation of Intermediate 18

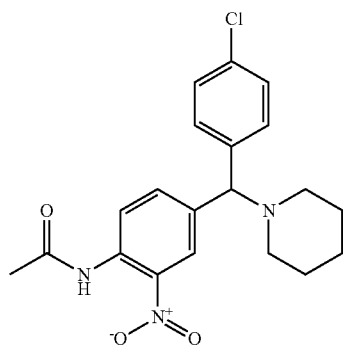

A mixture of intermediate 17 (0.088 mol), piperidine (0.446 mol) and potassium carbonate (0.442 mol) in acetonitrile (250 ml) with a small amount of KI was stirred at 40° C. for 12 hours and the solvent was evaporated (vac.). The residue was taken up in water and the mixture was extracted with DCM. The organic layer was dried (MgSO$_4$) and the solvent was evaporated dry. The residue was purified by liquid chromatography over silica gel (eluent: DCM). The product fractions were collected and the solvent was evaporated, yielding 16 g (47%, oil) of intermediate 18.

e) Preparation of Intermediate 19

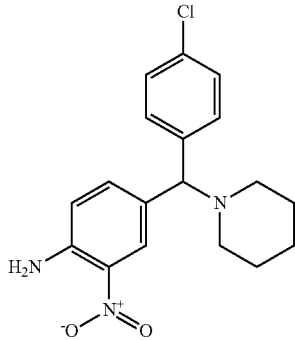

A mixture of intermediate 18 (0.0413 mol) in sodium hydroxide (1.5N) (160 ml) and THF/methanol (10 ml) was stirred for 48 hours at room temperature, then the solution was neutralised to pH: 7, extracted with EtOAc and washed with water. The organic layer was dried (MgSO$_4$) and the solvent was evaporated dry. The oily residue (12.5 g) was purified by high-performance liquid chromatography over silica gel (eluent: DCM/CH$_3$OH 99/1). The product fractions were collected and the solvent was evaporated, yielding 10 g (71%) of intermediate 19, melting point 124° C.

h) Preparation of Intermediate 20

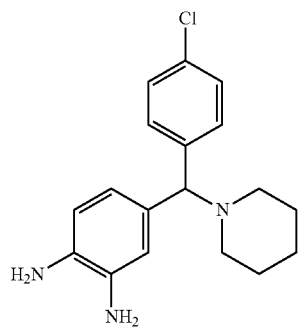 [SMILES: Nc1ccc(C(c2ccc(Cl)cc2)N2CCCCC2)cc1N]

A mixture of intermediate 19 (0.0289 mol) in methanol (200 ml) was hydrogenated for 2 hours with Raney Nickel (10 g) as a catalyst. After uptake of H$_2$ (3 equiv.), the solution was filtered over a celite path. yielding 9.1 g of intermediate 20 (used as such in the next reaction step without further purification).

B. Preparation of the Final Compounds

Example B1

Preparation of Compound 1

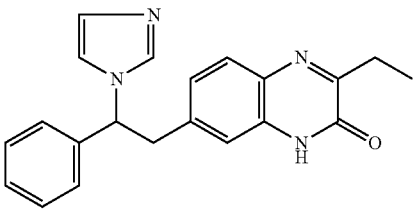 [SMILES: CCc1nc2ccc(CC(c3ccccc3)n3ccnc3)cc2[nH]c1=O]

A mixture of intermediate 6 (0.0089 mol) and ethyl 2-oxobutanoate (0.0178 mol) in methanol (50 ml) was stirred and refluxed for 15 hours, then cooled to room temperature, poured out into ice water and extracted with DCM. The organic layer was separated, dried (MgSO$_4$), filtered and the solvent was evaporated till dryness. The residue (3.1 g) was purified by column chromatography over silica gel (15-40 μm) (eluent: toluene/2-propanol/NH$_4$OH 85/15/0.8). The desired fractions were collected and the solvent was evaporated. The residue was purified by column chromatography over silica gel (15-40 μm)(eluent: toluene/2-propanol/NH$_4$OH 85/15/0.8). The pure fractions were collected and their solvents were evaporated. The residue (0.3 g) was crystallized from 2-propanone and diethyl ether. The precipitate was filtered off and dried, yielding 0.3 g (10%) of compound 1, melting point 166° C.

Example B2

Preparation of Compound 2

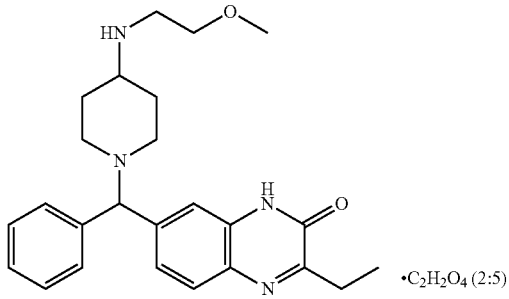 [SMILES: CCc1nc2ccc(C(c3ccccc3)N3CCC(NCCOC)CC3)cc2[nH]c1=O]

·C₂H₂O₄ (2:5)

A mixture of intermediate 9 (0.0043 mol), intermediate 10 (0.0052 mol) and potassium carbonate (0.0129 mol) in acetonitrile (15 ml) was stirred at 80° C. for 15 hours, then cooled to room temperature, poured out into ice water and extracted with EtOAc. The organic layer was separated, dried ($MgSO_4$), filtered and the solvent was evaporated till dryness. The residue (2.2g) was purified by column chromatography over silica gel (15-40 μm) (eluent: DCM/$CH_3OH$/$NH_4OH$ 95/5/0.2). The pure fractions were collected and the solvent was evaporated. The residue (0.27g) was dissolved in 2-propanone and converted into the ethanedioic acid salt (2:5). The precipitate was filtered off and dried, yielding 0.25g of compound 2, melting point 98° C.

Example B3

Preparation of Compound 3

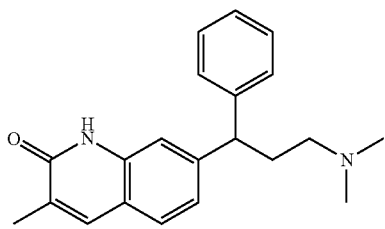

Intermediate 14 (0.0107 mol) in methanol (60 ml) was hydrogenated with Pd/C 10% (0.36 g) as a catalyst for 16h under a 3 bar pressure. After uptake of $H_2$ (1 eq), the catalyst was filtered through celite and the filtrate was evaporated till dryness. The residue (3.58 g) was purified by column chromatography over silica gel (15-40 μm) (eluent: DCM/$CH_3OH$/$NH_4OH$ 93/7/0.5). The pure fractions were collected and the solvent was evaporated. The residue (1.45 g) was crystallized from methyl ethyl keton. The precipitate was filtered off, washed with diethylether and dried, yielding 0.82 g (30%) of compound 3.

Example B4

Preparation of Compound 4

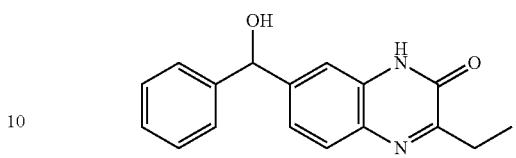

Sodium hydroborate (0.0719 mol) was added at 0° C. under $N_2$ flow to a suspension of intermediate 7 (0.0719 mol) in methanol (300 ml) and THF (100 ml). The mixture was stirred for 30 min and poured out into ice water. The precipitate was filtered off, washed with water and dried. A part (0.7 g) of this fraction (8.33 g) was crystallized from methanol and water. The precipitate was filtered off and dried, yielding 0.59 g of compound 4, melting point 202° C.

Example B5

Preparation of Compound 5

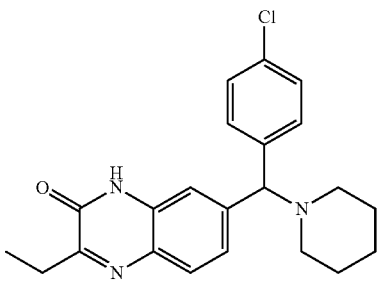

A solution of 2-oxo-butanoic acid (0.0294 mol) in acetic acid (30 ml) was added to a solution of intermediate 20 (0.0288 mol) in water (70 ml) at 0° C. and the reaction mixture was stirred for 2 hours at 0° C. The resulting solution was poured out into ice-water, neutralised with sodium hydroxide (3N) and extracted with DCM. The organic layer was dried ($MgSO_4$) and the solvent was evaporated dry. The residue was purified by liquid chromatography over silica gel (eluent: toluene/2-propanol/$NH_4OH$ 90/10/0.1). Two product fractions were collected and the solvent was evaporated. The upper fraction after purification was crystallised from diethylether/DCM/MEK and the desired product was collected, yielding 1.15 g of compound 5.

Table F-1 lists the compounds that were prepared according to one of the above Examples. The following abbreviations were used in the tables: Co.No. stands for Compound Number, Ex. [Bn°] referred to the same method as described in the Bn° examples.

TABLE 1
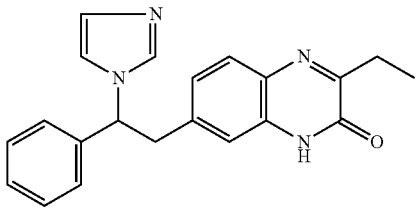
Co. No. 1; Ex. [B1]; mp. 166° C.
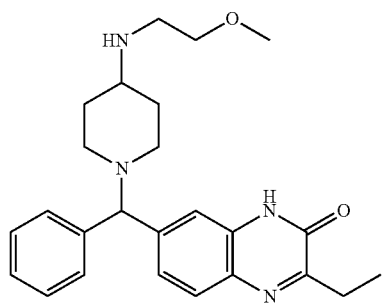
C₂H₄O₄ (2:5) Co. No. 2; Ex. [B2]; mp. 98° C.
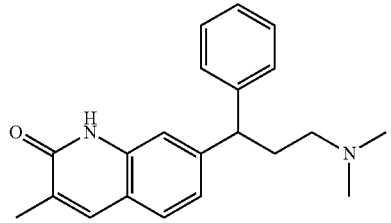
Co. No. 3; Ex. [B3]
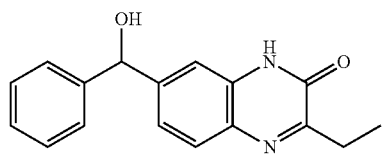 [SMILES: CCc1nc2ccc(C(O)c3ccccc3)cc2[nH]c1=O]
Co. No. 4; Ex. [B4]; mp. 202° C.
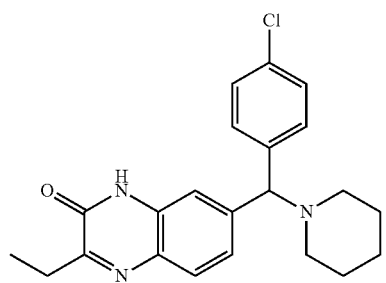
Co. No. 5; Ex. [B5]
TABLE 1-continued
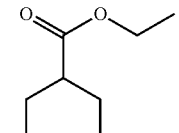
Co. No. 6; Ex. [B1]; mp. 182° C.
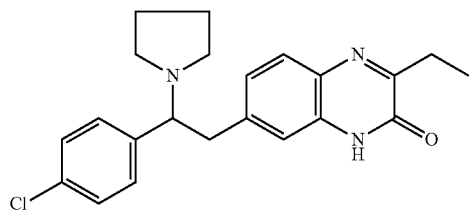
Co. No. 7; Ex. [B1]; mp. 176° C.
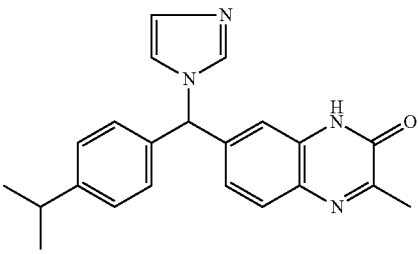
Co. No. 8; Ex. [B1]; mp. 210.4° C.
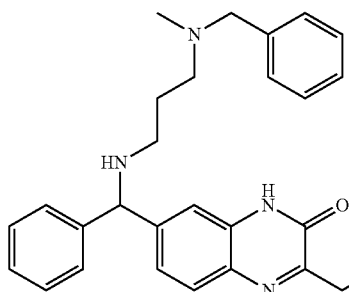
C₂H₄O₄ (1:2) Co. No. 9; Ex. [B2]; mp. 118° C.
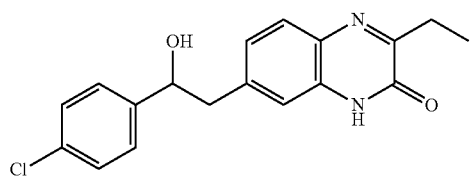
Co. No. 10; Ex. [B4]; mp. 254° C.

TABLE 1-continued

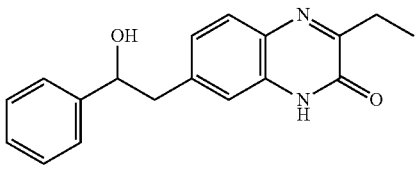

Co. No. 11; Ex. [B4]; mp. 202° C.

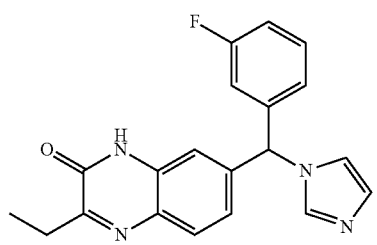

Co. No. 12; Ex. [B5]; mp. 174.6° C.

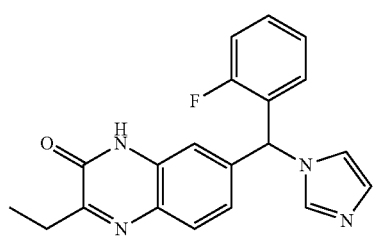

Co. No. 13; Ex. [B5]; mp. 203.1° C.

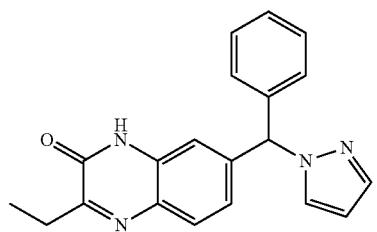

Co. No. 14; Ex. [B5]; mp. 230° C.

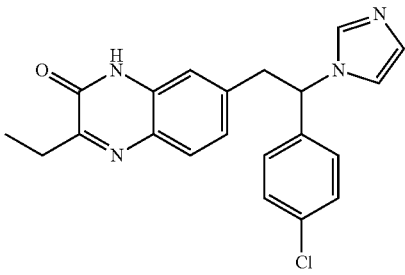

Co. No. 15; Ex. [B5]; mp. 184° C.

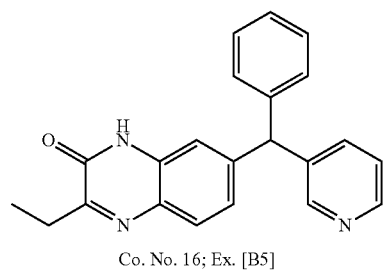 [SMILES: CCc1nc2ccc(C(c3ccccc3)c3cccnc3)cc2[nH]c1=O]

Co. No. 16; Ex. [B5]

TABLE 1-continued

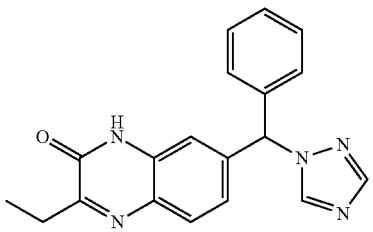

Co. No. 17; Ex. [B5]; mp. 264.4° C.

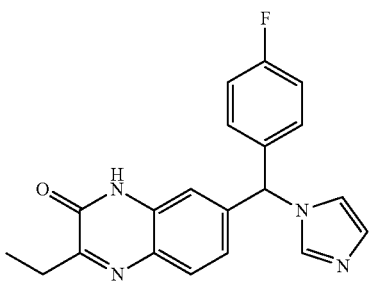

Co. No. 18; Ex. [B5]; mp. 118° C.

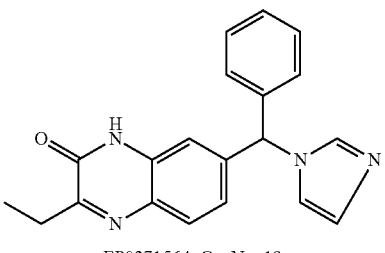

EP0371564; Co. No. 19

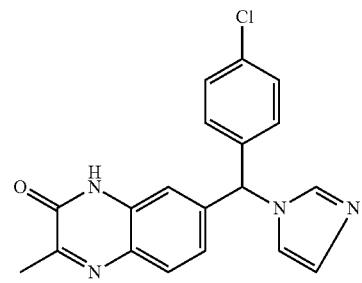

EP0371564; Co. No. 20

Pharmacological Example

In vitro Scintillation Proximity Assay (SPA) for PARP-1 Inhibitory Activity

Compounds of the present invention were tested in an in vitro assay based on SPA technology (proprietary to Amersham Pharmacia Biotech).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^+$) as ADP-ribosyl donor.

As inducer of PARP-1 enzyme activity, nicked DNA was prepared. For this, 25 mg of DNA (supplier: Sigma) was dissolved in 25 ml DNAse buffer (10 mM Tris-HCl, pH 7.4; 0.5 mg/ml Bovine Serum Albumine (BSA); 5 mM MgCl$_2$.

6H$_2$O and 1 mM KCl) to which 50 µl DNAse solution (1 mg/ml in 0.15 M NaCl) was added. After an incubation of 90 min. at 37° C., the reaction was terminated by adding 1.45 g NaCl, followed by a further incubation at 58° C. for 15 min. The reaction mixture was cooled on ice and dialysed at 4° C. for respectively 1.5 and 2 hours against 1.5 l of 0.2 M KCl, and twice against 1.5 l of 0.01 M KCl for 1.5 and 2 h respectively. The mixture was aliquoted and stored at −20° C. Histones (1 mg/ml, type II-A, supplier: Sigma) were biotinylated using the biotinylation kit of Amersham and stored aliquoted at −20° C. A stock solution of 100 mg/ml SPA poly(vinyl toluene) (PVT) beads (supplier: Amersham) was made in PBS. A stock solution of [$^3$H]-NAD$^+$ was made by adding 120 µl of [$^3$H]-NAD$^+$ (0.1 mCi/ml, supplier: NEN) to 6 ml incubation buffer (50 mM Tris/HCl, pH 8; 0.2 mM DTT; 4 mM MgCl$_2$). A solution of 4 mM NAD$^+$ (supplier: Roche) was made in incubation buffer (from a 100 mM stock solution in water stored at −20° C.). The PARP-1 enzyme was produced using art known techniques, i.e. cloning and expression of the protein starting from human liver cDNA. Information concerning the used protein sequence of the PARP-1 enzyme including literature references can be found in the Swiss-Prot database under primary accession number P09874. Biotinylated histones and PVT-SPA beads were mixed and pre-incubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^+$ was added per well into a 96-well microtiterplate. The final concentrations in the incubation mixture were 2 µg/ml for the biotinylated histones, 2 mg/ml for the PVT-SPA beads, 2 µg/ml for the nicked DNA and between 5-10 µg/ml for the PARP-1 enzyme. After incubation of the mixture for 15 min. at room temperature, the reaction was terminated by adding 100 µl of 4 mM NAD$^+$ in incubation buffer (final concentration 2 mM) and plates were mixed.

The beads were allowed to sediment for at least 15 min. and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of 10$^{-6}$M. When the compounds showed activity at 10$^{-6}$M, a dose-response curve was made wherein the compounds were tested at concentrations between 10$^{-5}$M and 10$^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the SPA assay. The tested compounds showed inhibitory activity at the initial test concentration of 10$^{-6}$M (see Table-2).

In vitro Filtration Assay for PARP-1 Inhibitory Activity

Compounds of the present invention were tested in an in vitro filtration assay assessing PARP-1 activity (triggered in the presence of nicked DNA) by means of its histone poly (ADP-ribosyl)ation activity using [$^{32}$P]-NAD as ADP-ribosyl donor. The radioactive ribosylated histones were precipitated by trichloroacetic acid (TCA) in 96-well filterplates and the incorporated [$^{32}$P] measured using a scintillation counter A mixture of histones (stock solution: 5 mg/ml in H$_2$O), NAD (stock solution: 100 mM in H$_2$O), and [$^{32}$P]-NAD$^+$ in incubation buffer (50 mM Tris/HCl, pH 8; 0.2 mM DTT; 4 mM MgCl$_2$) was made. A mixture of the PARP-1 enzyme (5-10 µg/ml) and nicked DNA was also made. The nicked DNA was prepared as described in the in vitro SPA for PARP-1 inhibitory activity. Seventy-five µl of the PARP-1 enzyme/DNA mixture together with 1 µl of compound in DMSO and 25 µl of histones-NAD$^+$/[$^{32}$P]-NAD$^+$ mixture was added per well of a 96-well filterplate (0.45 µm, supplier Millipore). The final concentrations in the incubation mixture were 2 µg/ml for the histones, 0.1 mM for the NAD$^+$, 200 µM (0.5 µC) for the [$^{32}$P]-NAD$^+$ and 2 µg/ml for the nicked DNA. Plates were incubated for 15 min. at room temperature and the reaction was terminated by the addition of 10 µl ice cold 100% TCA followed by the addition of 10 µl ice-cold BSA solution (1% in H$_2$O). The protein fraction was allowed to precipitate for 10 min. at 4° C. and plates were vacuum filtered. The plates were subsequently washed with, for each well, 1 ml of 10% ice cold TCA, 1 ml of 5% ice cold TCA and 1 ml of 5% TCA at room temperature. Finally 100 µl of scintillation solution (Microscint 40, Packard) was added to each well and the plates were transferred to a TopCount-NXT™ (supplier: Packard) for scintillation counting and values were expressed as counts per minute (cpm). For each experiment, controls (containing PARP-1 enzyme and DMSO without compound), a blank incubation (containing DMSO but no PARP-1 enzyme or compound) and samples (containing PARP-1 enzyme and compound dissolved in DMSO) were run in parallel. All compounds tested were dissolved and eventually further diluted in DMSO. In first instance, compounds were tested at a concentration of 10$^{-5}$M. When the compounds showed activity at 10$^{-5}$M, a dose-response curve was made wherein the compounds were tested at concentrations between 10$^{-5}$M and 10$^{-8}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the filtration assay. The tested compounds showed inhibitory activity at the initial test concentration of 10$^{-5}$M (see Table-2).

TABLE 2

| Co. No. | In vitro SPA pIC50 | In vitro filtration assay pIC50 |
|---|---|---|
| 1 | 6.687 | |
| 2 | 8.125 | |
| 3 | 6.046 | 5.005 |

TABLE 2-continued

| Co. No. | In vitro SPA pIC50 | In vitro filtration assay pIC50 |
|---|---|---|
| 4 | 6.388 | |
| 5 | 6.628 | 6.159 |
| 6 | 6.087 | |
| 7 | 6.232 | |
| 8 | 6.386 | 5.852 |
| 9 | 6.506 | |
| 10 | 6.258 | |
| 11 | 6.039 | |
| 12 | 6.138 | 5.444 |
| 13 | 6.144 | 5.306 |
| 14 | 5.797 | 5.573 |
| 15 | 6.483 | 5.195 |
| 16 | 6.239 | 5.344 |
| 17 | 6.476 | |
| 18 | 6 | 5.384 |
| 19 | 6.636 | 6.211 |
| 20 | 5.386 | <5.000 |

The compounds can be further evaluated in a cellular chemo- and/or radiosensitization assay, an assay measuring inhibition of endogenous PARP-1 activity in cancer cell lines and eventually in an in vivo radiosensitization test.

The invention claimed is:

1. A combination of a compound with a chemotherapeutic agent wherein said compound is a compound of

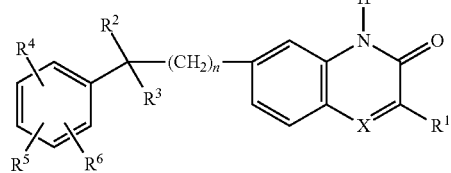

(I)

an N-oxide form, a pharmaceutically acceptable salt or a stereo-chemically isomeric form thereof, wherein
n is 0, 1 or 2;
X is N or $CR^7$, wherein $R^7$ is hydrogen;
$R^1$ is $C_{1-6}$alkyl;
$R^2$ is hydrogen, hydroxy, $C_{1-6}$alkyl, or $C_{3-6}$alkynyl;
$R^3$ is a radical selected from —$(CH_2)_s$—$NR^8R^9$ (a-1), —O—H (a-2), or —O—$R^{10}$ (a-3), wherein
s is 0, 1, 2 or 3;
$R^8$ and $R^{10}$ are each independently selected from —CHO, $C_{1-6}$alkyl, hydroxy$C_{1-6}$alkyl, $C_{1-6}$alkylcarbonyl, amino, $C_{1-6}$alkylamino, di($C_{1-6}$alkyl)amino $C_{1-6}$alkyl, $C_{1-6}$alkyloxycarbonyl, $C_{1-6}$alkylcarbonylamino $C_{1-6}$alkyl, piperidinyl, piperidinyl$C_{1-6}$alkyl, piperidinyl$C_{1-6}$alkylaminocarbonyl, $C_{1-6}$alkyloxy, thienyl$C_{1-6}$alkyl, pyrrolyl$C_{1-6}$alkyl, aryl$C_{1-6}$alkylpiperidinyl, arylcarbonyl$C_{1-6}$alkyl, arylcarbonylpiperidinyl$C_{1-6}$alkyl, haloindozolylpiperidinyl$C_{1-6}$alkyl, or aryl$C_{1-6}$alkyl($C_{1-6}$alkyl)amino$C_{1-6}$alkyl; and
$R^9$ is hydrogen or $C_{1-6}$alkyl;
or $R^3$ is a group of formula —$(CH_2)_t$—Z— (b-1), wherein
t is 0, 1, 2 or 3;
Z is a heterocyclic ring system selected from

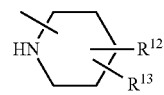
(c-1)

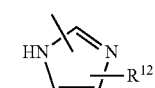
(c-2)

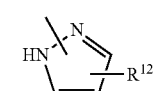
(c-3)

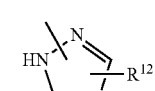
(c-4)

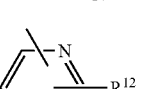
(c-5)

or

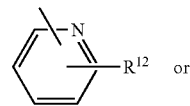
(c-11)

wherein each $R^{12}$ independently is hydrogen, halo, $C_{1-6}$alkyl, aminocarbonyl, amino, hydroxy, aryl,

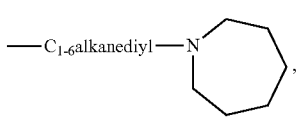, 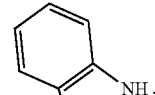

$C_{1-6}$alkylamino$C_{1-6}$alkyloxy, $C_{1-6}$alkyloxy$C_{1-6}$alkyl, $C_{1-6}$alkyloxy$C_{1-6}$alkylamino, aryl$C_{1-6}$alkyl, di(phenyl)$C_{1-6}$alkenyl, piperidinyl, piperidinyl$C_{1-6}$alkyl, $C_{3-10}$cycloalkyl, $C_{3-10}$cycloalkyl$C_{1-6}$alkyl, aryloxy (hydroxy)$C_{1-6}$alkyl, haloindazolyl, aryl$C_{1-6}$alkyl, aryl$C_{2-6}$alkenyl, aryl$C_{1-6}$alkylamino, morpholino, $C_{1-6}$alkylimidazolyl, or pyridinyl$C_{1-6}$alkylamino;
each $R^{13}$ independently is hydrogen, piperidinyl or aryl;
$R^4$, $R^5$ and $R^6$ are each independently selected from hydrogen, halo, trihalomethyl, trihalomethoxy, $C_{1-6}$alkyl, $C_{1-6}$alkyloxy, amino, amino$C_{1-6}$alkyl, di($C_{1-6}$alkyl)amino, di($C_{1-6}$alkyl)amino$C_{1-6}$alkyloxy or $C_{1-6}$alkyloxycarbonyl, or $C_{1-6}$alkyl substituted with 1, 2 or 3 substituents independently selected from hydroxy, $C_{1-6}$alkyloxy, or amino$C_{1-6}$alkyloxy;
aryl is phenyl or phenyl substituted with halo, $C_{1-6}$alkyl or $C_{1-6}$alkyloxy.

* * * * *